United States Patent [19]
Wilcko et al.

[11] Patent Number: 6,109,916
[45] Date of Patent: Aug. 29, 2000

[54] ORTHODONTIC METHOD AND DEVICE

[76] Inventors: M. Thomas Wilcko, 6074 Peach St.; William M. Wilcko, 6066 Peach St., both of Erie, Pa. 16509

[21] Appl. No.: 09/164,604

[22] Filed: Oct. 1, 1998

Related U.S. Application Data

[60] Provisional application No. 60/061,072, Oct. 3, 1997, and provisional application No. 60/075,073, Feb. 18, 1998.

[51] Int. Cl.[7] .................................................. A61C 3/00
[52] U.S. Cl. ................................................. 433/24; 433/7
[58] Field of Search ....................................... 433/7, 8, 24

[56] References Cited

U.S. PATENT DOCUMENTS

| | | | |
|---|---|---|---|
| 4,347,054 | 8/1982 | Kraus et al. ................................ | 433/7 |
| 4,354,832 | 10/1982 | Wallshein ................................... | 433/7 |
| 4,433,956 | 2/1984 | Witzig ........................................ | 433/7 |
| 4,482,318 | 11/1984 | Förster ....................................... | 433/7 |
| 4,483,674 | 11/1984 | Schütz ....................................... | 433/7 |
| 5,002,485 | 3/1991 | Aagesen .................................... | 433/7 |
| 5,281,133 | 1/1994 | Farzin-Nia ................................. | 433/7 |
| 5,439,377 | 8/1995 | Milanovich ................................ | 433/7 |
| 5,472,344 | 12/1995 | Binder et al. .............................. | 43/7 |

OTHER PUBLICATIONS

Jan L. Wennstrom, Mucogingival Considerations in Orthodontic Treatment, Seminars in Orthodonitcs, Mar., 1996, pp. 46–54, vol. 2, No. 1.

G. G. Steiner, et al., Changes of the Marginal Periodontium as a Result of the Labial Tooth Movement in Monkeys, Journal Periodontal, Jun., 1981, pp. 314–320.

Heinrich Wehrbein, et al., Mandibular Incisors, Alveolar Bone and Symphysis After Orthodontic Treatment. A Retrospective Study, American Journal of Orthodontics and Dentofacial Orthopedics, Sep., 1996, pp. 239–246.

Naphtall Brezniak, M.D., et al., Root Resorption After Orthodontic Treatment: Part 1. Literature Review, American Journal of Orthodontics and Dentofacial Orthopedics, p. 62, vol. 103, No. 2.

Naphtall Brezniak, M.D., et al., Root Resorption After Orthodontic Treatment: Part 2. Literature Review, American Journal of Orthodontics and Dentofacial Orthopedics, p. 138, vol. 103, No. 2.

R. Riedel, Review of the Retention Problem, American Journal of Orthodontics, 1960, pp. 179–199, vol. 30.

(List continued on next page.)

*Primary Examiner*—Nicholas D. Lucchesi
*Attorney, Agent, or Firm*—Edward W. Goebel, Jr.; MacDonald, Illig, Jones and Britton LLP

[57] ABSTRACT

Teeth within a patient's mouth are moved by an orthodontic method of treatment in which orthodontic appliances are installed at a desired time during the treatment on the teeth to be moved. Cortical bone adjacent the roots of the teeth to be moved is partially decorticated. Bone grafting material is installed between the partially decorticated cortical bone and the mucoperiosteum. The orthondontic appliances are adjusted thereafter as needed to move the teeth toward the positions desired. One orthodontic appliance which can be used for applying orthopedic force between a patient's anterior teeth on one side of an edentulous area and a patient's posterior teeth on the other side includes a front body, a back body and a screw member operatively connected between them. The screw member is adjustable to cause the front body and the back body to move away from one another and to move toward one another while transmitting an orthopedic force between them. At least one slide rod extends between the front body and the back body and is slidable through at least one of these as they move toward and away from one another. The front body is coupled to at least one anterior tooth and the back body is coupled to at least one posterior tooth so as to transmit the orthopedic force between these teeth as the screw member is adjusted.

5 Claims, 10 Drawing Sheets

OTHER PUBLICATIONS

R. C. Thurow, Edgewise Orthodontics, 1966, pp. 258–274, 2nd Ed., St. Louis: The C.V. Mosby Company.

Wendy Sharpe, et al., Orthodontic Relapse, Apical Root Resorption, and Crestal Alveolar Bone Levels, American Journal of Orthodontics and Dentofacial Orthopedics, 1987, pp. 252–258, vol. 91, No. 3.

George V. Newman, et al., Mucogingival Orthodontic and Periodontal Problems, American Journal of Orthodontics and Dentofacial Orthopedics, Apr. 1994, pp. 321–327, vol. 105, No. 4.

Heinrich Köle, M.D., Surgical Operations on the Alveolar Ridge to Correct Occlusal Abnormalities; Oral Surgery, Oral Medicine and Oral Pathology, May 1959, p. 515, vol. 12.

William H. Bell, D.D.S. and Barnet M. Levy, D.D.S., Revascularization and Bone Healing After Maxillary Corticotomies, Journal of Oral Surgery, Sep. 1972, pp. 640–648, vol. 30.

Jürgen Düker, Experimental Animal Research Into Segmental Alveolar Movement After Corticotomy, Journal of Maxillofacial Surgery, 1975, pp. 81–84, vol. 3, No. 2.

Hajime Suya, Corticotomy in Orthodontics; DRS. Ernst Hösl and Anton Baldauf (authors), Mechanical and Biological Basics in Orthodontic Therapy; 1991, pp. 207–226, Hüthig Book Verlag GmbH, Heidelberg, Germany.

J. Milford Anholm, D.D.S., M.S., et al., Corticotomy–facilitated Orthodontics, California Dental Association Journal, Dec. 1986, p. 8.

Bernard Gantes, et al., Effects on the Periodontium Following Corticotomy–Facilitated Orthodonitcs. Case Reports, Journal of Periodontology, Apr. 1990, p. 234, vol. 4.

Robert S. Goldie and Gregory J. King, Root Resorption and Tooth Movement in Orthodontically Treated, Calcium–Deficient and Lactating Rats, American Journal of Orthodontics, May 1984, pp. 424–430, vol. 85, No. 5.

Hwai–Nan Chang, et al., Angiogenic Induction and Cell Migration in an Orthopedically Expanded Maxillary Suture in the Rat, Archives of Oral Biology, 1996, pp. 985–996, vol. 41, No. 10.

Darwin J. Prockop, Marrow Stromal Cells as Stem Cells for Nonhematopoietic Tissues, Science, Apr. 1997, pp. 71–74, vol. 276, No. 4.

Avinoam Yaffe, et al., Regional Accelerated Phenomenon in the Mandible Following Mucoperiosteal Flap Surgery, Journal Periodontal, Jan. 1994, pp. 79–83.

Carl E. Misch, D.D.S., M.D.S. et al., Bone–Grafting Materials in Implant Dentistry, Inplant Dentistry, pp. 158–167, vol. II, No. 3.

Yoichiro Shigeyama, et al., Commercially–Prepared Allograft Material Has Biological Activity In Vitro, Journal Periodontal, Jun. 1995, pp. 478–487.

Anthony D. Viazis, *Atlas of Orthodontics: Principles and Clinical Applications*, W. B. Saunders Company, pp. 205–213, 1993.

James A. McNamara, Jr., et al., *Orthodontic and Orthopedic Treatments in the Mixed Dentition*, Needham Press, pp. 131–144, 1993.

T. D. Foster, *A Textbook of Orthodontics*, Blackwell Scientific Publications, 2nd Edition, pp. 246–261, 1982.

William R. Proffit, et al., *Contemporary Orthodontics*, The C. V. Mosby Company, pp. 272–286.

Chester S. Handelman, Nonsurgical Rapid Maxillary Alveolar Expansion in Adults: A Clinical Evaluation, The Angle Orthodontic, 1997, pp. 291–305, vol. 67, No. 4.

Samir E. Bishara, et al., Maxillary Expansion: Clinical Implications, Am. J. Orthod. Dentofac. Orthop., 1987, pp. 3–14, vol. 91, No. 1.

Bjorn U. Zachrisson, DDS, MSD, PHD, Important Aspects of Long–Term Stability, JCO, Sep., 1997, pp. 562–583.

Thorkild Karring, et al., Bone Regeneration in Orthodontically Produced Alveolar Bone Dehiscences, Journal of Periodontal Research 17: 309–315, 1982.

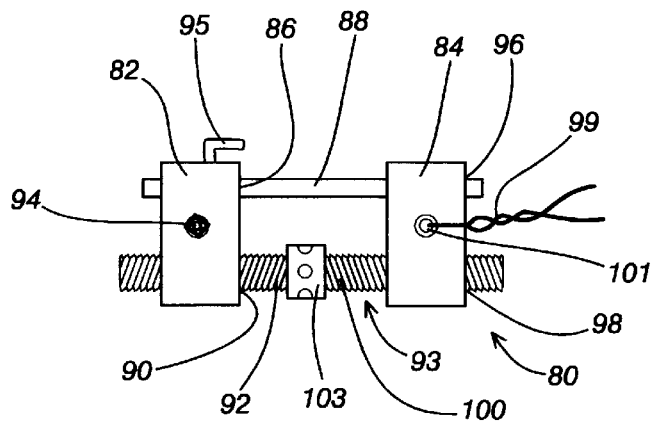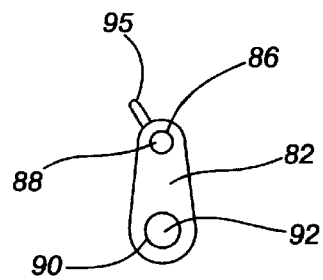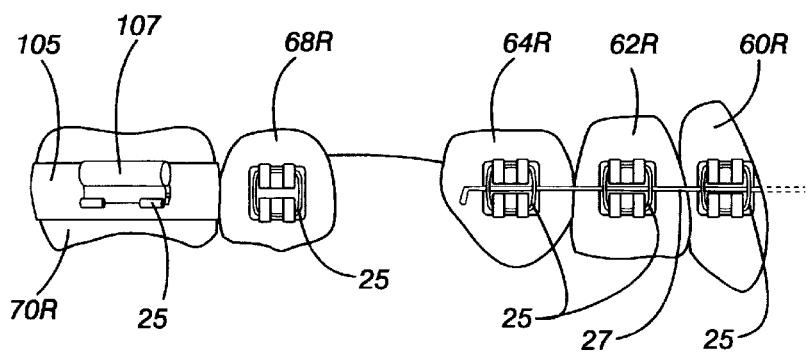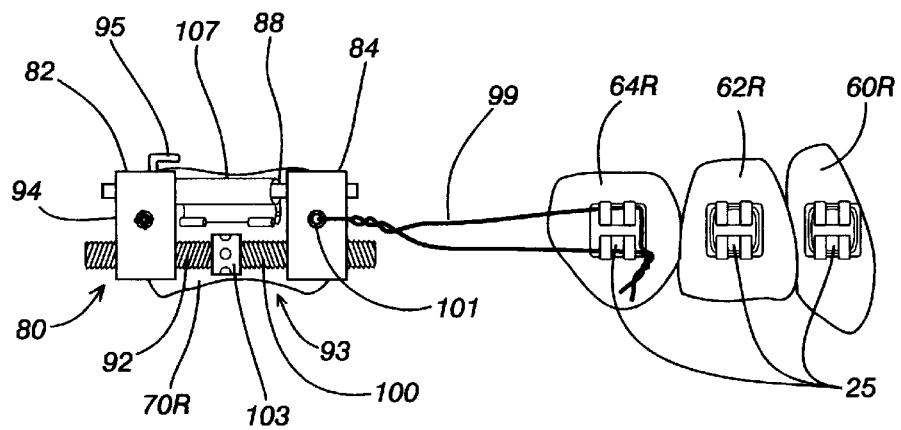

ORTHODONTIC METHOD AND DEVICE

This patent application is a continuation-in-part of provisional patent application Ser. No. 60/061,072 filed on Oct. 3, 1997 by M. Thomas Wilcko and William M. Wilcko and entitled Orthodontic Method and 60/075,073, filed Feb. 18, 1998.

BACKGROUND OF THE INVENTION

This invention relates to a method of performing dental procedures, and more particularly, to a method of performing orthodontic procedures and a device useful in performing some of those procedures.

Orthodontic cases are generally divided into two categories according to the direction in which the major tooth movements are made to straighten the teeth. The first category will be referred to as expansion cases. In expansion cases the crowded and crooked teeth are moved toward the periphery of the outline of the jawbone to make room for them. The second category will be referred to as retraction cases. In retraction cases generally one or more teeth are removed to create more room in the jaw for the teeth that remain. To line them up straight, the teeth that have been retained are then moved in the direction of the spaces created by the tooth removal. These two categories are a very gross division of orthodontic cases and there can be overlapping between them. For example, in a retraction case there may also be some expansion of teeth toward the periphery of a jaw to aid in the straightening. There are also other types of movements such as rotational movements, finishing movements, etc., that are routinely included in both expansion and retraction cases.

Conventional orthodontics is accomplished by moving the root of a tooth through its surrounding bone in the jaw of a patient. The bone of the jaw is similar to the long bones in one's arms and legs in that there is a hard outer shell, called the cortical plate or cortical bone, and a softer interior called the medullary bone. FIG. 1 shows a typical cross-section of a long bone in which a cortical plate 20 surrounds medullary bone 22.

The medullary bone has a good blood supply and is highly populated with pluripotential cells that can convert to osteoclasts that resorb old bone and osteoblasts that make new bone. It is this vital nature of the medullary bone which gives it the ability to respond in a dramatic and timely fashion to physical insult, such as the forces used to move teeth. To move a tooth orthodontically, the root of the tooth must be moved through the bone surrounding the tooth. This is called the alveolar bone, which consists of the medullary bone as well as the surrounding cortical plates which comprise the upper and lower jaws, also called dental arches. The alveolar bone remodels around a tooth being moved in response to pressure from one side of the tooth, as the tooth is being pressed against the alveolar bone on that side during movement, and in response to tension from the opposite side of the tooth as the tooth tends to move away from the alveolar bone on that side. Theoretically, in the course of this bone remodeling process, bone resorption, that is a loss of bone, occurs on the pressure side of the root surface in the direction in which the tooth is being moved. Bone deposition, also called apposition or new bone formation or build-up, takes place on the tension side of the root surface, that is the direction away from which the tooth is being moved.

Conceptually, it would seem that the roots of the teeth should move rapidly during conventional orthodontic treatment since they extend down into the jawbone and would seemingly be surrounded by the softer and more vital medullary bone. FIG. 2 shows a cross section of an upper front tooth comprising central incisor 24 having an orthodontic appliance such as a bracket 25 installed on it. The central incisor 24 is surrounded by a periodontal ligament 26 which attaches the root of the tooth to the alveolar bone. The medullary bone 22 is covered by the cortical plate 20, which is in turn is covered by gum or gingival tissue 28.

Unfortunately, the root of a typical tooth 24 is usually so large in diameter that it takes up most of the space between the lingual cortical plate on the inside of the jaw and the facial cortical plate on the outside of the jaw. This is especially true with respect to the anterior teeth, that is teeth in the front of the mouth. Little, if any, room is left for the soft inner, medullary bone. As a result, much of the root of a tooth is covered with the hard cortical plate and with very little soft medullary bone as is shown in FIG. 3. Compared to medullary bone, the cortical plate has a greatly reduced blood supply and a negligible complement of pluripotential cells. This greatly reduces the ability of the cortical plates to remodel during the course of orthodontic treatment.

To maintain the same initial thickness of the alveolar bone over the inside and outside prominences of the root during the tooth movement, the corresponding inner and outer surfaces of the alveolar bone must thicken and thin, respectively. Thus as the alveolar bone adjacent to the pressure side of the root surface resorbs and the alveolar bone adjacent to the tension side of the root surfaces builds-up, the corresponding inner and outer surfaces of the alveolar bone must thicken and thin, respectively, as shown in FIG. 4. The arrows 30 indicate the direction in which the tooth is being moved. The dots, some of which are marked 32, indicate areas where the bone is being resorbed. The dark areas 34 indicate where new bone is being formed. Unfortunately, this process does not always occur as predictably as desired.

Recent studies have shown that when a tooth is moved a significant distance there is a tendency to lose the alveolar bone over the prominence of the root especially in the direction in which the tooth is being moved. This tendency to lose alveolar bone and to consequently expose the surface of the root of a tooth is called dehiscence formation. See, by way of example, a study by Jan L. Wennstrom entitled "Mucogingival Considerations in Orthodontic Treatment," published in *Seminars in Orthodontics*, Vol. 2, No. Mar. 1, 1996: pgs. 46–54; a study by G. G. Steiner, et al., entitled "Changes of the Marginal Periodontium as a Result of the Labial Tooth Movement in Monkeys," *Journal Periodontal*, June, 1981, pp. 314–20; "Mandibular Incisors, Alveolar bone and Symphysis After Orthodontic Treatment. A Retrospective Study," by Heinrich Wehrbein, et al., published in *American Journal of Orthodontics and Dentofacial Orthopedics*, September 1996, pp. 239–46.

As shown in FIG. 5, this loss of alveolar bone over the prominence of the root, or dehiscence formation, is particularly significant near the neck of a tooth 35 where the root is usually the widest in diameter and the overlying cortical plate is likely to be thin. The above studies have shown that the periodontal ligament and the alveolar bone recede along the prominence of the root to an area 33 more apical, that is toward the tip of the root of the tooth, than is normal. Thus, gum or gingival tissue 28 covers the root of the tooth without having any alveolar bone between it and the tooth. In other words, in the direction the tooth is being moved, the tooth is literally pushed into a position outside the periphery of the jaw bone. This results in a decrease in bony support for the tooth.

The potential for a dehiscence formation is more of a problem with teeth undergoing orthodontic treatment that are overlapped and crowded as shown in FIG. 6. To correct the crooked alignment of the teeth 29, the teeth must be expanded or moved toward the outside of the jaw, as shown by the arrows 30, to make room for them. FIG. 7 shows the final position of the teeth 29 after they have been straightened. The incisors 36 and 38, the premolar 40 and the molars 42 and 44 may all be moved facially, or outward, from their starting positions in FIG. 6 to their final position in FIG. 7 to complete the straightening process. Each of these teeth is susceptible to developing a dehiscence as shown in FIG. 5 where the alveolar bone has migrated apically over the prominence of the root.

Another undesirable sequela that can occur as a consequence of conventional orthodontics is referred to as apical root resorption. Apical root resorption refers to a situation in which the tip of the root resorbs. This root resorption can vary from slight to severe. As a result the root is shorter following the completion of the orthodontic work. Apical root resorption is a function of not only pressure but time. That is to say, the longer it takes to complete the orthodontic work, the more root resorption that can potentially be expected. One can typically expect to see more root resorption in an adult than in an adolescent. As an individual ages, there is often more of a tendency for the root to resorb in preference to the bone which surrounds it. This is generally attributed to the fact that with aging the cortical plates tend to thicken and even the medullary bone tends to become less vital, that is the blood supply decreases, and the marrow spaces become smaller and the fat content increases.

FIG. 8 shows a typical single-rooted tooth prior to having undergone orthodontic movement. Note the length of the tooth from its apex 46 to the tip 48 of its crown. FIG. 9 shows a reported condition of a tooth some time after it has undergone conventional orthodontic movement. Note that apical root resorption has significantly decreased the distance between the apex 46a of this tooth and the tip 48a of its crown. This has resulted in an unfavorable crown-to-root ratio. The length of the crown is now greater than the length of the root. Severe root resorption can lead to irreversible mobility of the teeth and at times even the loss of the teeth themselves. Apical root resorption as a result of conventional orthodontics was reported by Naphtall Brezniak, et al. in the *American Journal of Orthodontics and Dentofacial Orthopedics*, Vol. 103, No. 2, beginning at p. 62 in an article entitled "Root Resorption After Orthodontic Treatment: Part 1. Literature Review", and continuing at p. 138 in an article entitled "Root Resorption After Orthodontic Treatment: Part 2 Literature Review."

For orthodontic treatment to be considered successful, the completed case must remain stable. If in the years that follow the completion of the orthodontic work the teeth move and become crooked again, the case is considered to have relapsed. If a case relapses, all of the time and money that was invested in the orthodontic treatment was wasted. Orthodontic relapse is not an uncommon problem, especially when expansion is used to accomplish the desired major orthodontic movements. It has been stated that adequate root length and adequate bony support around the roots are important factors in the maintenance of post-treatment stability. See, by way of example, "Review of the Retention Problem," by R. Riedel, *American Journal of Orthodontics*, Vol. 30, 1960, pp. 179–99: and *Edgewise Orthodontics*. 2nd ed. St. Louis: The C.V. Mosby Company, R. C. Thurow, 1966, pp. 258–74. It has also been suggested that there may indeed be a relationship between orthodontic relapse and the parameters of increased root resorption. See, by way of example, "Orthodontic Relapse, Apical Root Resorption, and Crestal Alveolar Bone Levels," by Wendy Sharpe, et al., *American Journal of Orthodontics and Dentofacial Orthopedics*, Vol. 91, No. 3, 1987, pp. 252–58. Both apical root resorption and dehiscence formation result in less root surface in the bone at the completion of conventional orthodontic work than was present prior to starting the orthodontic work. Consequently, with less alveolar bone supporting the roots of the teeth, there is an increased risk that the completed case will relapse and fail.

Dehiscence formation not only predisposes a tooth to relapse, but it also predisposes a tooth to gingival recession. If due to a dehiscence forming there is now a lack of alveolar bone between the gingiva and the adjacent root surface, there is an increased tendency for the gingiva to recede, thereby exposing the root of the tooth. See, by way of example, "Mucogingival Considerations in Orthodontic Treatment" by Wennstrom, above, at p. 50; "Changes in Marginal Periodontium as a Result of the Labial Tooth Movement in Monkeys," by Steiner, et al., above, at pp. 317–20; and "Mucogingival Orthodontic and Periodontal Problems," by George V. Newman, et al., *American Journal of Orthodontics and Dentofacial Orthopedics*, Vol. 105, No. 4, April 1994, pp. 321–27.

A major drawback to conventional orthodontics is the long treatment time during which braces must be worn, which generally ranges from one to three years. Wearing braces for this period of time, is neither pleasant nor popular. Unfortunately, for reasons such as perceived social restrictions, many adults and adolescents alike decline orthodontic treatment. Those patients who accept treatment almost always look longingly to the day when their braces will be removed. The most frequent question asked of any orthodontist is, "When will my braces be taken off." Thus, shortening orthodontic treatment durations is desirable if it can be accomplished without jeopardizing the quality of the final result. Several attempts have been made to shorten the treatment time but have not adequately addressed the problem of dehiscence formation in the bone over the prominences of the roots as a consequence of orthodontic treatment.

A surgical procedure called corticotomy has been employed for several decades to attempt to shorten orthodontic treatment times. But corticotomy has been reported to have been used only following the cessation of growth in post-adolescents and adults. For the purpose of consistency and clarity the use of the term osteotomy will indicate a bony cut that extents through the entirety of the portion of the jawbone supporting a tooth, that is alveolus. This would include the outer or facial cortical plate, the softer inner medullary bone, and inside or lingual cortical plate. The term corticotomy will indicate a bony cut or perforation that extends through the entire thickness of the cortical plate of the alveolus and just barely into the underlying medullary bone. If there is no medullary bone under the cortical plate, a corticotomy will also refer to a bony cut or perforation that extends through most of the thickness of the cortical plate, but not its entire thickness. The lack of medullary bone is often encountered over the prominences of the roots, especially of the anterior or front teeth, and more so closer to the necks of the teeth where the roots are widest in diameter.

In the journal *Oral Surgery, Oral Medicine and Oral Pathology*, Vol. 12, May 1959, at page 515, Dr. H. Köle wrote an article entitled "Surgical Operations on the Alveolar Ridge to Correct Occlusal Abnormalities" in which he describes the use of the corticotomy in orthodontic tooth movement in humans. There are other references in the literature dating back to the late 1800's, but Köle is generally credited with the introduction of this procedure. Köle emphasized that the main resistance to tooth movement is encountered in the continuous cortical layer. He suggested that this is likely attributable to the slower remodeling process in the cortical bone as compared to the much faster remodeling capabilities of the medullary bone. He reasoned that by disrupting the continuity of the cortical layer, the speed of the tooth movement could be greatly increased. To gain access to the cortical layer of bone, it was necessary to reflect full thickness gingival, or mucoperiosteal, flaps. But in doing so, the blood supply from the overlaying mucoperiosteum was disrupted. Köle speculated that by leaving medullary bone mostly intact, it would act as the nutritive pedicle, that is a vascular pathway, to the denuded bone and prevent an avascular phenoma, or lack of blood flow leading to necrosis, in the surgerized alveolar bone. Köle's objective was to create blocks or segments of bone in which a tooth or group of teeth was embedded and which were connected to each other and to other structures through only the medullary bone. In a manner of speaking, the crowns of the teeth then became the handles by which the segments of bone could be moved somewhat independently of each other with the applied orthodontic forces. He theorized that the rapid tooth movement that resulted was due to the lack of resistance of the soft medullary bone.

However, when Köle introduced the corticotomy it was used in conjunction with osteotomies in both expansion and retraction scenarios. To promote expansion of the teeth toward the periphery of the outline of the jaw, he made vertical and horizontal cuts in the alveolar process both facially arid lingually to create the bony blocks or segments. The vertical cuts were made interdentally, that is between the teeth, and were done in the manner of a corticotomy. That is, these cuts penetrated the entire thickness of the cortical layer and extended only barely into the medullary bone. The vertical cuts started interproximally between the crowns of adjacent teeth and extended well beyond the apices of the teeth. These vertical cuts were then joined beyond the apices with a horizontal cut. The horizontal cut, however, was performed in the manner of an osteotomy, that is to say that it penetrated the entire thickness of the alveolus to include the facial cortical plate, the lingual cortical plate, and the interposed medullary bone. In the upper posterior areas, these horizontal osteotomies penetrated the Schneiderian membrane, which is the membrane which lines the maxillary sinuses. The only horizontal cut that was not performed in the manner of an osteotomy was in the lower posterior areas. The neural and vascular innervation of the lower posterior areas preclude such a cut. In the lower posterior areas the connecting horizontal cut was performed in the manner of a corticotomy. In retraction cases Köle utilized a wide vertical osteotomy in the extraction sites, leaving only a thin layer of medullary bone over the adjacent root surfaces. It appears that most of the orthodontic movements were accomplished with removable appliances that were to be worn continually and only removed briefly for cleaning.

Köle claimed that most of the cases were completed in 12 weeks or less. Upon examination of the cases he reported, it seems that the fine finishing movements that are typically employed today before an orthodontic case would be considered completed were absent. The orthodontic movements, which Köle completed in 12 weeks or less, were rather gross major movements.

Köle claimed that leaving the medullary bone intact prevented devitalization of the teeth and also prevented injury to the periodontium and pocket formation. He also attributed a lack of root resorption to the notion that it is not the tooth itself that was displaced, but rather the alveolar block in which the tooth was embedded. He also suggested that the healing of the cortical cuts should prevent relapse. It is most important to note that Dr. Köle makes no mention of luxation, or dislocation, of individual dentoalveolar blocks in an attempt to mobilize them.

In the *Journal of Oral Surgery*, volume 30, September 1972, pp. 640–48, William H. Bell and Barnet M. Levy wrote an article entitled "Revascularization and Bone Healing After Maxillary Corticotomies". In this article they questioned the appropriateness of the one-stage corticotomy procedure as presented by Köle in 1959. One-stage refers to the reflection of facial and lingual full thickness flaps in the same area during the same surgical procedure. They expressed concern that the resulting dentoalveolar blocks, which are for a short period of time deprived of the mucoperiosteal blood supply, might not receive an adequate blood supply through the rather small amount of remaining interconnecting medullary bone. To test their theory, one-stage maxillary corticotomies were performed bilaterally in the premolar and incisor regions in four rhesus monkeys. From their results, they concluded that the one-stage maxillary corticotomies had a disruptive effect on the maxillary central incisors. In particular there was a damaging effect to the periodontium around these teeth. It was noted that at nine weeks post-surgery, there was gross ischemia or a lack of oxygen carrying material of the blood supply due to the interruption of the blood supply, in much of the alveolar bone surrounding the coronal portion of the incisor roots and within the surrounding periodontal vascular plexuses.

Bell and Levy, however, did not follow the protocol as described by Köle. The vertical interdental cuts were corticotomies as described by Köle. But rather than connecting the vertical corticotomies beyond the apices of the teeth with a horizontal osteotomy, they used a corticotomy. Of most notable importance is that the resulting dentoalveolar segments were immediately mobilized by malleting a chisel between the corticotomy sites. Bell and Levy admitted that the immediate mobilization of each dentoalveolar segment likely replaced the corticotomies in a number of areas with complete interdental osteotomies. This would have most certainly had a negative effect on the circulation in these areas. Köle, as mentioned above, did not recommend the mobilization of the dental alveolar segments.

In the Journal of Maxillofacial Surgery, Volume 3, No. 2, 1975, pp. 81–4, Jürgen Düker wrote an article entitled "Experimental Animal Research into Segmental Alveolar Movement after Corticotomy" in which he repeated Köle's procedure fairly closely to the way it was described in 1959. Six male beagle dogs were utilized. Vertical corticotomies were preformed between the upper central incisors and upper lateral incisors. No vertical corticotomy was performed between the two upper central incisors. The two vertical corticotomies were then connected beyond the apices with a horizontal osteotomy. With the use of very thick rubber bands, the segment of bone with the two central incisors was displaced about 4 mm in 8–20 days. The rubber bands were attached to a heavy facial arch wire which also served to hold the upper lip away from the incisors during the segmental movement. The use of this type of device would not be practical in humans.

Düker did keep the vertical corticotomies somewhat shy of the marginal bone. He theorized that by doing so there would be less of a chance of damaging the marginal periodontium. He concluded that rapid movement performed in this manner does not damage the vasculature supplying the dental pulps. He further noted that clear vascular changes were found in the marginal gingiva. Düker also observed that two of the dogs had developed slightly deepened periodontal pockets. He felt that this was of minimal consequence and by keeping the vertical corticotomies short of the alveolar crest significant damage in this regard could be avoided. Like Köle, Düker did not report mobilization of the dentoalveolar segments by luxation.

H. Suya wrote a chapter entitled "Corticotomy in Orthodontics" at pp. 207–26 of *Mechanical and Biological Basis in Orthodontic Therapy*, edited by Drs. Ernst Hösl and Anton Baldauf and published by Huthig Book Vertag GmbH of Heidelberg, Germany in 1991. Dr. Suya first traced the history of corticotomy. He described corticotomy on page 208 of his chapter as a surgical technique "in which a fissure is made through the cortical bone (compact bone) that surrounds a tooth so that the tooth is embedded within a block of bone that is connected to adjacent blocks through only the medullary bone. In this way, the tooth plays the role of the handle by which the bands of less dense medullary bone are moved block-by-block. In other words, the orthodontic tooth movement in corticotomy is a process of moving blocks rather than moving only the teeth themselves."

At page 216 Suya described the orthodontic and surgical procedures involved in corticotomy-assisted orthodontics. This included securing the orthodontic brackets to the teeth prior to the surgical portion of the treatment. The actual surgery was initiated by intracrevicular incisions around the necks of the teeth with subsequent reflection of full thickness gingival flaps to gain access to the cortical bone overlying the roots of the teeth to be moved. He advocated not using vertical releasing incisions at the opposite ends of the flaps to prevent the trapping of air inside the flaps at the time of flap replacement and suturing. The cortical plates were completely exposed both facially and lingually beyond the apices of the teeth. The corticotomy cuts were a combination of vertical and horizontal grooves that were made both facially and lingually around the teeth to be moved. The vertical interdental cuts began 2 to 3 millimeters below the alveolar crest, as recommended by Düker, and extended beyond the apices of the teeth, as recommended by Köle. The horizontal cuts were made beyond the apices of the teeth and connected the interdental vertical cuts. In this respect Suya differed from Köle, who used a horizontal osteotomy rather than the horizontal corticotomy, except on the facials of the lower posterior teeth where Köle also used a horizontal corticotomy.

In paragraph 7 on page 216 Suya stated: "These resections are made on both facial and lingual sides so that the block of bone thereby created, is now retained by only medullary bone. Resistance to the tooth movements is now obviously reduced." At the conclusion of the surgery the full thickness gingival flaps were returned to their original positions and secured by continuous suture. In all examples given Suya performed the surgery at two different sittings, that is, the upper arch at one session and the lower arch at another session. Like Köle, Suya did not mobilize the resulting dentoalveolar segments by luxation. Suya inserted and activated the archwire connected to the brackets on the teeth immediately following the completion of the surgery. A packing material dripping with disinfectant was then placed around the necks of the teeth. Suya recommended making the periodic orthodontic adjustments at 10 to 14 day intervals until the treatment goal was accomplished. Suya claims to have treated hundreds of post-adolescent and adult Japanese patients since 1972. He reportedly limited the usage of the corticotomy assisted orthodontics to post-adolescents and adults, since in these patients the rapid growth period was ended and movement was limited to the dentoalveolar element. Suya reported that 69% of the time stage II orthodontic movements were completed within 127 days. Although Suya gave examples in which different malocclusions were treated, they were apparently all treated through expansion. He gave no examples in which extractions with subsequent retraction of the teeth were employed. Suya was insistent that the rapid tooth movement which followed the corticotomy surgery was attributable to the movement of the resulting dentoalveolar blocks and not to the movement of the teeth through the surrounding alveolar bone. Since in the "dentoalveolar block movement hypothesis" the tooth and the block of bone in which it was embedded were thought to move in unison, there was no expressed concern that the tooth was being moved to a position outside the periphery or limits of the alveolar bone, which would result in dehiscence formation over the prominences of the root. This set the stage for some erroneous assumptions, two of which were that the completed case would be more stable and that bone grafting was not needed. More specifically, in Table 7 on Page 210 of this chapter, Dr. Suya specifically states that corticotomy orthodontics "(N)egates the need for a bone grafting procedure." J. Milford Anholm, et al. reported in the *California Dental Association Journal*, Dec. 1986 edition, beginning at page 8, on research conducted at the Loma Linda University School of Dentistry on corticotomy in an article entitled "Corticotomy-facilitated Orthodontics." They traced a history of corticotomy procedures and credited their research in this field since 1983 to Dr. Suya's encouragement and assistance. The procedure that they described is substantially the same as that used by Dr. Suya. After explaining the vertical and horizontal cuts made in the cortical bone, Dr. Anholm, et al. stated "These resections are made both facially and lingually so that the tooth is now connected only through medullary bone and resistance to movement is greatly reduced." They gave one case report in which a 23 year old male with a severe malocclusion was treated by non-extraction and expansion. This case was completed in 11 months. They listed as one of the many unanswered questions about corticotomy-facilitated orthodontics "(H)ow much tooth movement is actually accomplished with the bone movement?" They reported that most orthodontic cases can be completed in a year or less with this method.

The research at Loma Linda University School of Dentistry was further reported by Bernard Gantes, et al., in an article entitled "Effects on the Periodontium Following Corticotomy-Facilitate Orthodontics, Case Reports," beginning at page 234 of Volume 4 of the April 1990 edition of the *Journal of Periodontology*. In the four adult cases that were used in the final statistical analysis, it appears that extractions with subsequent retraction were employed. As Köle recommended in 1959 the extraction sites were osteotomized to create spaces in which to move the adjacent teeth that were being retracted. Orthodontic forces were employed. They reported a mean treatment time of 14.8 months for their corticotomy-facilitated orthodontic patients, as compared with 28.3 months for the conventional orthodontic treatment controls. They reported no significant adverse clinical periodontal effects.

Gantes et al., did, however, report noticeable apical root resorption as evidenced on the post-treatment periapical radiographs. As indicated above, Dr. Suya did not report significant apical root resorption when treating cases with expansion. No additional information was provided by Gantes, et al., concerning the amount of tooth movement that was actually accomplished with segmental movement of the dentoalveolar blocks. Due to the increased appliance complexity and the frequency of patient visits, they estimated the total chair time for the corticotomy patients to be approximately the same as that for the conventional orthodontic controls.

RESEARCH LEADING UP TO THIS INVENTION

To attempt to ascertain why teeth can be moved more rapidly following a corticotomy procedure, we decided to duplicate some of the protocols referred to above. In the final analysis we decided to repeat the pure corticotomy protocol as performed by Dr. Suya in expansion cases. We also decided to repeat the corticotomy with complete osteotomizing of the extraction sites that was presented by Gantes, et al., in retraction cases that were treated at Loma Linda with the instruction and assistance of Dr. Suya. The corticotomy portion of these two protocols can be used in all areas of the dentition with relative ease and safety.

We borrowed the vertical osteotomy that was used in the extraction sites by Gantes, et al., from Köle's protocol and was performed without significant risks to adjacent tissues. Our prime concern with Köle's protocol was that it called for a connecting osteotomy beyond the apices of the teeth. Performing the osteotomy in these areas is difficult and does involve some risk to adjacent tissues. Additionally the osteotomy cannot be used in the lower posterior areas due to the neurovascular innervation of these areas. After performing the supra-apical osteotomies as recommended by Köle, Düker reported increased pocket depths in two of the experimental beagles, which would indicate the potential for at least some degree of morbidity to the periodontium.

We selected one adult and one adolescent for treatment according to Suya's corticotomy assisted orthodontic expansion protocol. In one respect, this was a departure from the work of Suya and the others in that they only reported treating post-adolescents and adults. To the best of our knowledge we were the first to use and advocate the use of this procedure for adolescents.

We performed pure corticotomies around the teeth of both patients which were to be moved. These corticotomy cuts consisted of vertical interdental grooves starting just shy of the alveolar crest and ending beyond the apices of the teeth, plus horizontal grooves connecting the vertical grooves beyond the apices of the teeth. The dentoalveolar segments that we created were not mobilized. Our results were very much in agreement with Dr. Suya's results. As reported by Dr. Suya, no significant apical root resorption was noted. Dr. Suya reported completing the expansion cases on an average of 127 days. We completed our work on the adult in this study, from bracketing or placing braces to de-bracketing or removing braces in four and one-half months. The 14 year old adolescent in three months.

Even though our results were in agreement with Dr. Suya's results, our observations made and the conclusions reached concerning them were completely different. We took pre-treatment and post-treatment CT scans on the adult and on the adolescent. The post-treatment CT scan for the adult and the post-treatment CT scan for the adolescent showed significant dehiscence development over the prominences of the roots of the teeth that were expanded. The CT scans taken for the adult and for the adolescent prior to tooth movement did not show any dehiscences. There was absolutely no indication in the post-treatment CT scans that any block movement had taken place. In fact, what was seen on the post-treatment CT scans was exactly what would have been expected had these cases been treated with conventional orthodontics. We believe that the teeth in the corticotomy group were moving in a manner similar to conventional orthodontics tooth movement, but just at a faster rate.

Suya attributed the lack of significant apical root resorption to the notion that it was the block of bone in which the tooth was embedded which was undergoing the movement and not the root of the tooth moving through the surrounding alveolar bone. We discovered, as a result of the research leading up to this invention, that this is not the case. The corticotomies which we performed helped accelerate the remodeling process of the alveolar bone surrounding the roots, consequently making it possible for the roots to move through the alveolar bone faster and with decreased likelihood of root resorption. That is, the alveolar bone remodeled itself in preference to resorption of the roots of the teeth.

Previous studies have shown that an increase in the capability of the alveolar bone to remodel, will translate to a decrease in the likelihood of root resorption. See, by way of example, a study by Robert S. Goldie and Gregory J. King entitled "Root Resorption and Tooth Movement in Orthodontically Treated, Calcium-Deficient, and Lactating Rats", published in the *American Journal of Orthodontics*, Volume 85, No. 5, (May) 1984, pp. 424–30.

Previous studies have also indicated that blood vessel formation with accompanying pluripotential cells can exit the medullary bone if provided with a pathway. This will aid in the remodeling process of the alveolar bone. See, by way of example, a study by Hwai-Nan Chang, et al., entitled "Angiogenic Induction and Cell Migration in an Orthopedically Expanded Maxillary Suture in the Rat", published in *Archives of Oral Biology*, volume 41, No. 10, 1996, pp. 985–96.

It has also been reported that marrow stromal cells have pluripotential capabilities. That is, they can indeed act as the precursors in the development of other cell types, such as osteoblasts; which participate in the bone remodeling process. See, by way of example, a literature review by Darwin J. Prockop entitled "Marrow Stromal Cells as Stem Cells for Nonhematopoietic Tissues," published in *Science*, volume 276, No. 4, April 1997, pp. 71–4.

To further test the reported results of these studies, we selected another adult for treatment by corticotomy and expansion. We theoretically divided this patient's dentation in half so that the left half was treated with connecting corticotomy grooves as described by Suya and the right half was treated by pinpoint corticotomies so as not to disrupt the continuity of the cortical plates on the right side. Suya had reported, as indicated above, that it was the resistance offered by the continuity of the cortical plates that had to be overcome to speed tooth movement. If this were true, the teeth in the left side of this patient's dentition should have moved more rapidly than the teeth on the right side. This, however, proved not to be the case. The teeth on both sides expanded rapidly and at the same rate, further supporting our hypothesis that the rapid expansion of teeth with orthodontic forces following a corticotomy is attributable to an increase in the physiologic process of remodeling and not to block movement of dentoalveolar segments.

The assumption prior to our discovery had been that completed corticotomy cases would be more stable than conventional orthodontic cases, since the bone supposedly moved in unison with the roots of the teeth and the edges of the cortical cuts would fuse following the completion of the movement, forming a new, continuous cortical plate over the roots of the teeth. After we determined that this was not the case, but instead there was the likelihood of substantial dehiscence formation over the prominences of the roots of the teeth, we had to take into account the potential for relapse. There isn't much of an advantage to a patient if his or her orthodontic work is completed in a short period of time, but is equally prone to a risk of failure, that is relapse, as if it had been treated by slower, conventional orthodontic treatment.

RETRACTION

We selected one adult female, who was 22 years of age for orthodontic retraction in an attempt to duplicate the work of Gantes, Rathbun, and Anholm. This patient presented a mildly crowded Class II malocclusion with a severe dental overjet, sometimes called buck teeth. This was a pure retraction case, and no expansion was involved. This case was unusual in that no significant expansion was needed within the segment that was retracted or in the lower anterior arch. The upper first bicuspids were removed. As described by Gantes, Rathbun, and Anholm the extraction sites were completely osteotomized leaving only a thin layer of medullary bone over the root surfaces of the teeth adjacent the extraction sites. Pure facial and lingual corticotomies were then performed around the six teeth which remained in the anterior or frontal segment of bone. No surgery was required in the lower arch. Utilizing heavy orthodontic forces the upper anterior teeth were then retracted into the spaces created by the removal of the upper first bicuspids. This case did not proceed quickly and required about 13 months to complete, from bracketing to de-bracketing. This was, however, in close agreement with the average time of 14.8 months which had been reported by Gantes, Rathbun, and Anholm. There were no significant changes in the height of the alveolar bone around the six upper anterior teeth which were retracted.

Approximately 15 months following the initial surgery the upper anterior area was surgically re-entered. We did not find any significant dehiscence formation over the prominences of the roots of the six upper anterior teeth which had been retracted. The clinical appearance of the alveolar bone very closely resembled that of the CT scans. We attribute the absence of dehiscence formation to the lack of a need for expansion to correct this patient's teeth. Even though the thin layer of bone which was left over the root surface of the teeth adjacent the extraction sites still appeared to be intact, there was a rather deep indentation in the alveolar ridge where the osteotomies had been performed.

Examination of periapical radiographs of the anterior teeth of this patient showed several millimeters of apical root resorption. Gantes, et al, also reported apical root resorption in their patients. We hypothesized the long treatment times that were required were most likely responsible, at least in part, for the significant root resorption. We were concerned that this significant root resorption in the retraction cases could lead to instability and relapse.

The objects of this invention are to make it possible to complete the tooth movement in both expansion and retraction cases in a short period of time and to provide the patient with a healthy post-treatment periodontium to lessen the likelihood of gingival recession and relapse.

SUMMARY OF THE INVENTION

In accordance with this invention, teeth are moved to desired positions within a patient's mouth by a method which includes certain aspects of corticotomy-facilitated orthodontics. Reduced to its essentials, the method of this invention includes partially decorticating the cortical plates adjacent the teeth to be moved so as to access vasculature and pluripotential cells in the medullary bone or within the cortical bone and/or initiate regional accelerated phenomenon in the cortical bone adjacent teeth to be moved. Grafting material is permanently inserted between the partially decorticated cortical bone and adjacent mucoperiosteum which includes the gingiva. The term "grafting material" means any material or substance, with or without bone morphogenic proteins ("BMP's"), that can be converted to new bone or that can cause the generation of new bone. Grafting material also can include chemotactic attracting agents such as peptides which call cells to an area. These agents do not in themselves make the new bone, but attract cells to the area which lead to the new bone formation. Thereafter, orthodontic appliances installed on the teeth are adjusted as needed to move the teeth into the grafting material toward the desired positions.

The method of this invention described above can be accomplished in any manner found practicable. It will now be summarized in more detail with reference to the preferred embodiments. Orthodontic appliances are installed on the teeth to be moved to exert force on the teeth toward the desired positions. Normally, the orthodontic appliances are installed on the teeth within about one week prior to the surgical procedures, especially where orthodontic expansion is required within a patient's mouth. However, they can be installed on the teeth prior to or subsequent to the surgery as is desired by the dentists performing the surgical and orthodontic procedures.

According to the preferred embodiment of this invention, full thickness gingival flaps are reflected both facially and lingually to gain access to the bone around the teeth to be moved. Incisions are preceded by the normal premedication of a patient before the surgery and use of typical conscious intravenous sedation and local anesthesia as indicated. Thereafter an intracrevicular or sulcular incision is used, that is an incision in the space between the tooth and the gum. No vertical releasing incisions are needed. An attempt is also made to preserve the interdental papillae by reflecting the majority of each papilla with the lingual flap. However, this is not always feasible because of the crowding of the teeth and the resulting tight interproximal spaces that are present. An attempt is also made not to disturb any interdental soft tissue that may remain. The flaps are reflected beyond the apices, that is the tips of the roots, of the teeth. Care is taken to visualize any neurovascular bundles so these structures can be protected against damage.

After the full thickness gingival flaps have been reflected, the exposed cortical bone overlaying the roots of the teeth to be moved is partially decorticated both facially and lingually. The intent is to "activate" the cortical plates—that is to create bleeding points to stimulate blood vessel outgrowth and to create pathways into the medullary bone through which the pluripotential cells egress to promote the remodeling process of the cortical plates and to aid in the conversion of the grafting material into the patient's own bone. The decortication can take place through the use of vertical grooves made in the exposed facial and lingual cortical plates between the roots of the designated teeth. Additionally, or alternatively if desired and if there is sufficient thickness of bone, perforations can also be made in the cortical plates overlaying the roots of the teeth to be moved. In any event, the grooves and/or perforations must extend slightly into the underlying medullary bone wherever possible. The partial decortication is only performed around teeth that will undergo significant movement and is not done, to any significant extent, around orthodontic anchorage teeth, that is teeth that are used to resist movement. If decortication is performed mesial of the mental foramena, special care should be taken not to extend the cut more than just barely into the medullary bone so as to avoid hitting a potential anterior loop of the inferior alveolar nerve.

Grafting material is then spread over the partially decorticated plates. Immediately prior to the placement of the grafting material, any lip lubricant should be removed to avoid contamination of the grafting material. In spreading this material the objective is to achieve a fairly uniform layer of the desired depth. In one application of this invention a depth of approximately one and one-half to two millimeters was found to be appropriate. Use of excessive amounts of grafting material should be avoided because it compromises the repositioning and suturing of the mucoperiosteal flaps as described below.

The mucoperiosteal flaps are then replaced to their original positions and over the bone grafting material, using sutures to hold them in place. In so doing care should be taken to maintain the integrity of the layer of grafting material. This layer should be smoothed as the suturing progresses. According to the preferred embodiment of this invention, one or two sutures may be used in each interdental area to orient the flaps properly. Fairly large bites of the attached gingiva are taken with a suture needle. The sutures are drawn lateral to the center line of each interdental papilla, leaving the tips of the interdental papillae free to be pulled coronally. The coronal two millimeters of the margins of the sutured flaps which are coronal to the alveolar crest are then cleared of grafting material to aid in the readaptation of the gingiva to the cervical areas. So as not to encourage apical repositioning of the flaps, it is suggested that no periodontal dressing be used.

If orthodontic appliances have not been installed prior to the surgery they can be installed after surgery as desired. The orthodontic appliances, once activated, should be adjusted periodically, as needed, to move the teeth toward their desired positions. With this procedure there is a three to four month window of opportunity to complete the major orthodontic movements at an accelerated rate. After that point, the teeth move at conventional orthodontic rates. Thus, the orthodontic appliances must be adjusted frequently enough to complete the major orthodontic movements within the first two to four months of treatment. Satisfactory movement has occurred with adjustments approximately every two weeks.

Although there may be some minute movement of the segments of bone in expansion type cases, it is believed that the primary mode of action that creates the rapid tooth movements is the rapid remodeling process of the alveolar bone following the decortication process. Therefore, according to the method of this invention, orthodontic forces are sufficient to quickly move teeth in this type of case. An "orthodontic force" is an amount of force that, when applied to a tooth, allows the tooth to move through the surrounding bone by way of the resorption/deposition process described above.

Another type of force used in orthodontic treatments is called "orthopedic force." An orthopedic force is the amount of force that, when applied to teeth and/or surrounding bone, has the ability to move sections or segments of bone along with the adjacent teeth. Orthopedic forces are included in processes that enlarge, displace, lengthen, shorten, intrude, extrude, tip, torque, etc. sections or segments of bone.

Orthopedic forces are used, in accordance with one aspect of this invention, in situations where spaces are created by extraction of teeth or where excess spaces exist for whatever reason. It is often required to close these spaces to accomplish yöthe orthodontic objectives. When describing this aspect of the invention, this type of orthopedic retraction is referred to as osteogenic retraction, by which the anterior bony segment is pulled back distally and/or lingually. Osteogenic retraction is often needed, for example, when correcting an "overbite" or Class II malocclusion.

As further explained below, grafting material is placed in the spaces created by extraction prior to suturing. Otherwise, the orthodontic method is carried out as was explained, above.

A retraction device constructed in accordance with this invention can be used for applying orthopedic force between a patient's anterior teeth on one side of an edentulous area and a patient's posterior teeth on the other side of the edentulous area. The retraction device includes a front body and a back body and has a screw member which is operatively connected between them. The screw member is adjustable to cause the front body and the back body to move away from one another and to move toward one another while transmitting an orthopedic force between them. At least one slide rod extends between the front body and the back body and is slidable through at least one of these as the back body and front body move toward and away from one another. The retraction device is constructed in a manner which enables the front body to be coupled to at least one anterior tooth and the back body to be coupled to at least one posterior tooth so as to transmit an orthopedic force between the anterior tooth and the posterior tooth as the screw member is adjusted.

This invention does not reside in any one of the individual acts of the orthodontic method which are disclosed above or in the detailed description of the preferred embodiments or claimed below. Nor does this invention reside in the individual components of the orthodontic device disclosed. Rather, this invention is distinguished from the prior art by its combination of acts of the method disclosed. The combination of these surgical and orthodontic procedures is a clinically unique process. Additionally, the orthodontic device of this invention distinguishes from the prior art by the unique combination of components out of which it is constructed. Important features of this invention have been disclosed in the detailed description of the embodiments as shown and described below to illustrate the best mode contemplated to date for carrying out this invention.

BRIEF DESCRIPTION OF THE DRAWINGS

FIG. 38 is a top view of another retraction device made according to this invention;

FIG. 39 is a side view of the retraction device shown in FIG. 38;

FIG. 40 is a partial side view of a dental arch in which the retraction device shown in FIG. 38 can be installed;

FIG. 41 is a partial side view of a dental arch in which the retraction device shown in FIG. 38 is installed.

DESCRIPTION OF THE PREFERRED EMBODIMENT

Figure 1:
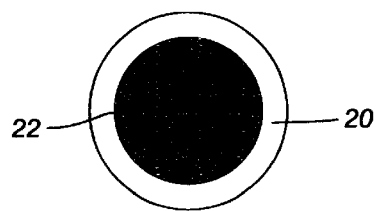
FIG. 1 is a cross section of a long bone.
Figure 2:
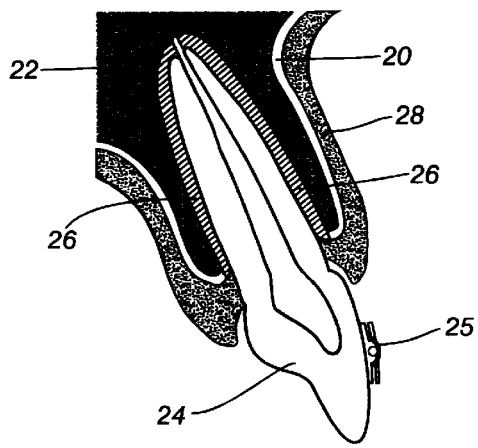
FIG. 2 is a cross section of an upper anterior tooth having an orthodontic appliance installed in it.
Figure 3:
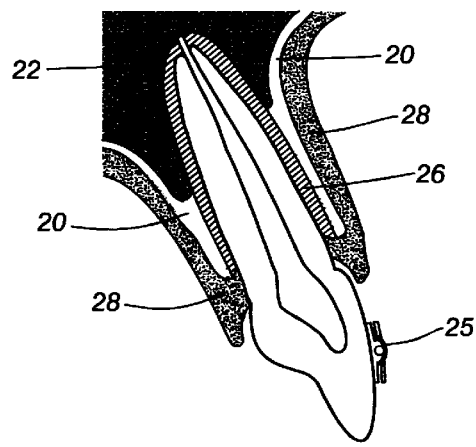
FIG. 3 is a cross section of an upper anterior tooth covered with cortical plate and a small amount of medullary bone.

Referring to the drawings, identical reference numerals and letters designate the same or corresponding items throughout the several figures shown in the drawings.

The orthodontic method of this invention can be used for both expansion and retraction cases and will be described with respect to each. All potential cases should be thoroughly evaluated first by an orthodontist and then by a periodontist to determine the feasibility of treatment. In this regard, conventional record taking used by both disciplines will suffice.

PATIENT EVALUATION

Patient conditions which are a cause for concern and might preclude the use of treatment by this method of invention or with conventional orthodontics are:

A. Substantial bone loss due to periodontal disease;
B. Significant furcation involvement as a result of periodontal disease;
C. Severe generalized gingival recession;
D. Anklylosed teeth, especially in adolescents;
E. Very short roots or unexplained root resorption;
F. Many missing teeth;
G. Restricted opening of the mouth;
H. A history of facial neuralgias;
I. A female who is pregnant or planning a pregnancy within the next 12 months;
J. Numerous teeth with cementomas;
K. Many teeth with extremely large and deep restorations;
L. Many non-vital teeth, with or without endodontic therapy;
M. An uncooperative patient; and
N. A patient with a medical or psychological condition which would negate the use of necessary surgery or medications that would be used in conjunction with or following the surgery.

As with conventional orthodontics there are additional patient conditions which must be corrected prior to treatment by this method of invention:

A. Periodontal disease;
B. Inadequate attached gingiva;
C. Carious areas or cavities;
D. Leaking restorations such as fillings;
E. Broken crowns; and
F. An endodontically involved tooth, where the pulp of the tooth has lost vitality.

It is preferable that an orthodontist and periodontist or oral surgeon share a very close working relationship, not only during treatment but in case selection and preparation for performing the orthodontic method of this invention. After the orthodontist has established that a case is suitable from an orthodontic standpoint, the periodontist must make sure that any other situation that could potentially jeopardize the case can be corrected.

Any active dental disease should be eliminated prior to commencing this orthodontic method. Periodontal disease, in particular, poses a very significant danger during the rapid tooth movement, especially as concerns the potential for apical migration of the epithelial attachment, that is pocket formation. An endodontically involved tooth must be determined to have undergone successful root canal treatment and any significant carious areas or cavities must be restored.

Perhaps the most critical and technique sensitive aspect of the surgery, and that which could have the greatest impact on post-treatment aesthetics, is the soft tissue manipulation, especially as concerns the reflection, repositioning and suturing of the flaps during surgery. An adequate zone of attached gingiva is essential, particularly around the anterior teeth, in helping to maintain the integrity of the flaps at closure. Any critical areas that are lacking in attached gingiva should be corrected with gingival grafting as a separate surgical procedure prior to employment of this method.

As listed earlier there are many situations that can preclude the use of the orthodontic method of this invention or certainly give cause for concern. Paramount among these would be the presence of one or more teeth that exhibit a smaller than normal amount of root surface in the alveolar bone. This situation may exist due to genetically short roots, trauma to the teeth which can initiate the root resorption process, or may result from substantial, untreated periodontal disease. Severe gingival recession may also indicate that there is a problem in this regard. Unexplained root resorption not only presents a diminished amount of root surface in bone, but may be an indication that the patient is extremely prone to root resorption, which could result in an even worse situation at the completion of the orthodontic work. Molars with furcation involvement due to bone loss present a different problem in that they are very prone to additional periodontal deterioration, even under ideal circumstances.

Teeth with compromised pulpal tissue (the central blood and nerve supply for the tooth) also present a different type of dilemma. As the dental pulp lays down secondary dentin in response to insult, the blood supply to the pulpal tissue becomes increasingly diminished. It is not inconceivable that the orthodontic forces could further compromise the blood supply to the pupal tissues and hasten their demise. It is difficult to ascertain the status of teeth that have previously received endodontic treatment. They may be perfectly healthy teeth and of no concern. On the other hand, there may be very minor deficiencies, such as a large unfilled lateral canal or microscopic perforation of the furcation, which was not apparent to the treating clinician and which the body has until now been able to contain, that with the additional trauma of the orthodontic forces become symptomatic.

Ankylosed teeth, that is teeth that have lost the PDL between the root surface and bone and have developed a hard tissue union in which the roots of the teeth are fused to the bone preventing movement, could present a significant problem if they are among the anterior teeth to be moved, and if they are to be kept following completion of the tooth movement. The orthodontic method of this invention may not be an additional benefit for ankylosed teeth as compared to conventional orthodontics. An ankylosed anterior tooth is even a bigger problem in an adolescent, compared to an adult. The adolescent patient's teeth are still erupting and his/her face and jaws all still growing, which presents a continually changing situation.

There can be no hard and fast rules concerning case selection since no two cases are identical. The professional must weigh the pros and cons and use his or her best judgement in this regard.

Orthodontic Method

Figure 10:
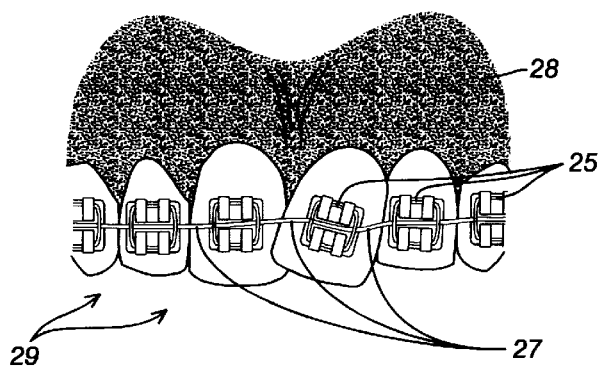
FIG. 10 shows upper anterior teeth after bracketing.
Figure 11:
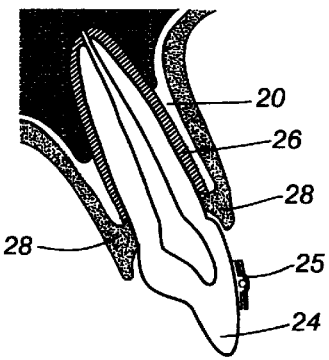
FIG. 11 is a cross section of an upper anterior tooth after bracketing.

As indicated above, in the course of the orthodontic method of this invention, orthodontic appliances are installed on the teeth to be moved to exert force on the teeth toward the desired positions. Any orthodontic appliances or auxiliaries, either fixed or removable, installed on teeth may be used in accordance with this invention, and for any orthodontic, orthopedic or surgical purpose. Referring to FIGS. 10 and 11, normally the orthodontic appliances 25 are installed c)n the teeth within about a week prior to the surgical procedures. They can, however, be installed on the teeth at anytime prior to the surgery or subsequent to it as desired by the dentists performing the surgical and orthodontic procedures. When the orthodontic method of this invention is used for a retraction case, to correct a Class II malocclusion, it was found that placing the orthopedic retracting devices following surgery was preferable.

FIGS. 10 and 11 show the upper anterior, or front, teeth after bracketing, that is the placing braces that are bonded to the teeth. The orthodontist decides where the anchorage units are needed and which teeth are to be moved in designated directions. The orthodontist, with the assistance of the periodontist or oral surgeon, then makes the decision as to where the decortications are to be made and the manner of decortications to be used. In FIGS. 10 and 11, the brackets 25 on the teeth 29 are connected with archwires 27. The gingival tissue 28 is still in place.

According to the preferred method of this invention, surgery is performed under intravenous sedation approximately two to seven days following activation of the brackets 25. Normally surgery is performed in both the upper and lower dental arch at one sitting, beginning with the lower arch, although surgery could be performed on one arch at a time if desired. The patient is pre-medicated in the normal manner prior to surgery. In a typical procedure, the patient is pre-medicated with 3 grams of penicillin one hour before surgery and 1.5 grams of penicillin six hours after the initial dose. The patient is then asked to take 250 mg of penicillin four times a day for the next 10 days or 250 mg of Augmentin three times a day for the next 10 days.

Figure 12:
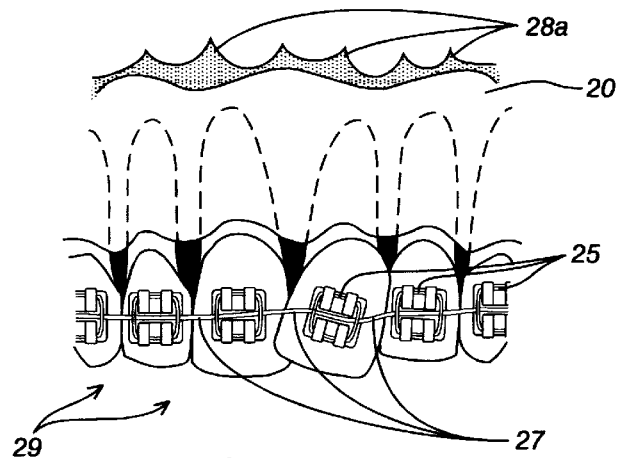
FIG. 12 shows upper anterior teeth with full thickness gingival flaps reflected.
Figure 13:
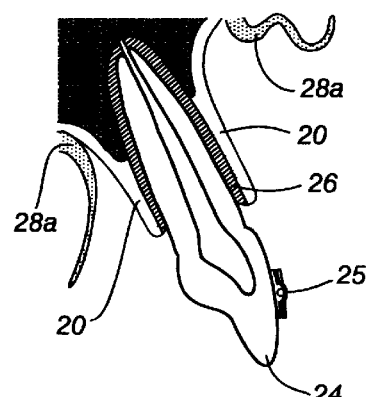
FIG. 13 is a cross section of an upper anterior tooth with full thickness gingival flaps reflected both facially and lingually.

In accordance with this invention, the cortical bone 20 adjacent the teeth to be moved must be partially decorticated so as to access vasculature and pluripotential cells in the medullary bone and/or stimulate regional accelerated phenomenon with respect to the cortical plate. Grafting material must then be permanently inserted between the partially decorticated cortical bone and adjacent mucoperiosteum which includes the gingiva. Any method of accomplishing these acts may be employed. Referring to FIGS. 12 and 13, the preferred method includes reflecting full thickness gingival flaps both facially and lingually around all of the teeth in the dental arch on which the operation is taking place. An intracrevicular incision is used, that is an incision in the space between the tooth and the gum, without employing a vertical incision. See the resulting full thickness gingival flaps 28a shown in FIGS. 12 and 13. As indicated above, the majority of the interdental papillae are reflected with the lingual flap in an attempt to preserve them. As shown in FIG. 13, the flaps 28a are reflected beyond the apices of the teeth. Care is taken to visualize any neurovascular bundles so these structures can be protected against damage.

Figure 14:
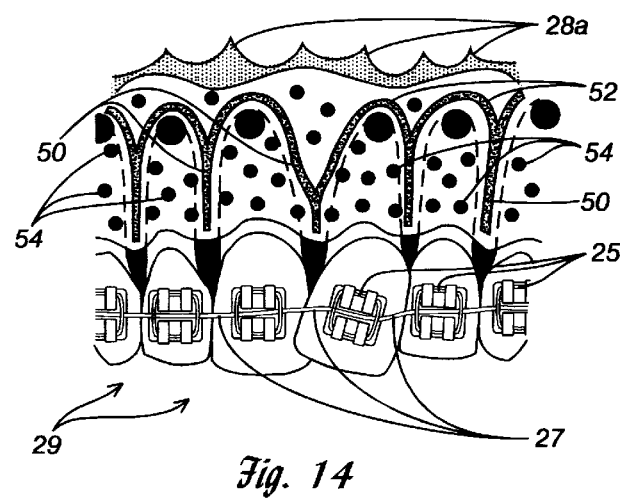
FIG. 14 shows upper anterior teeth with full thickness gingival flaps reflected and the exposed cortical plate partially decorticated.
Figure 15:
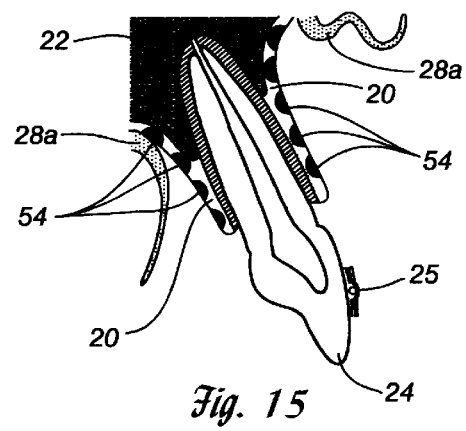
FIG. 15 is a cross section of an upper anterior tooth with full thickness gingival flaps reflected and exposed cortical plates partially decorticated.

Referring now to FIGS. 14 and 15, after the flaps have been reflected, the exposed cortical plate adjacent each of the teeth to be moved is partially decorticated. FIG. 14 shows that decortication takes place through the use of vertical grooves 50 shown in the exposed facial cortical plate between the roots of the designated teeth. Similar vertical grooves can be made in the exposed lingual cortical plates of the same teeth, as well. The vertical grooves 50 start slightly below the interdental crest and extend a couple of millimeters beyond the apices of the teeth where they are connected with scalloped horizontal grooves 52 of the type used in a pure corticotomy technique.

If there is sufficient thickness of bone, perforations 54 are also made in the cortical plates 20 overlying the roots of the teeth 24 as shown in FIGS. 14 and 15. The decorticating is performed with a #2 round bur mounted on a high speed handpiece with copious water irrigation. The grooves 50 and 52 and perforations 54 extend just slightly into the underlying medullary bone.

If decorticating is performed slightly mesial to the mental foremen, special care should be taken not to extend more than just barely into the medullary bone so as to avoid hitting a potential anterior loop of the inferior alveolar nerve. If the lining of a maxillary sinus is accidentally perforated, it can be plugged with a small piece of collagen prior to the use of grafting material.

Figure 16:
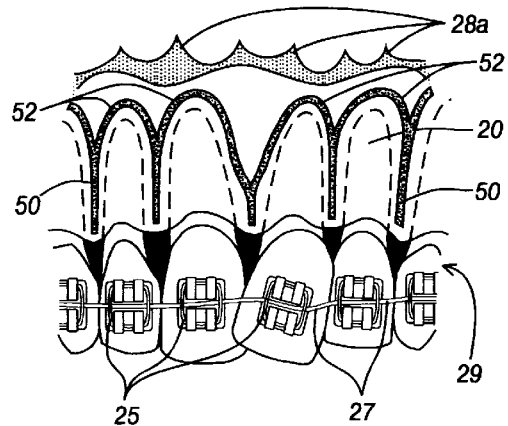
FIG. 16 shows upper anterior teeth with full thickness gingival flaps reflected and exposed cortical plate partially decorticated solely with grooves.

The cortical plate 20 can be activated through the use of both the grooves 50 and 52 and the perforations 54, as shown in FIGS. 14 and 15. The cortical plate 20 can also be sufficiently activated for the orthodontic method of this invention solely through the use of grooves 50 and 52, as shown in FIG. 16. The vertical grooves 50 and the scalloped horizontal grooves 52 connecting the vertical grooves 50 as shown in FIG. 16 are cut into the cortical plate in the same manner as the identically numbered grooves shown in FIG. 14.

Figure 17:
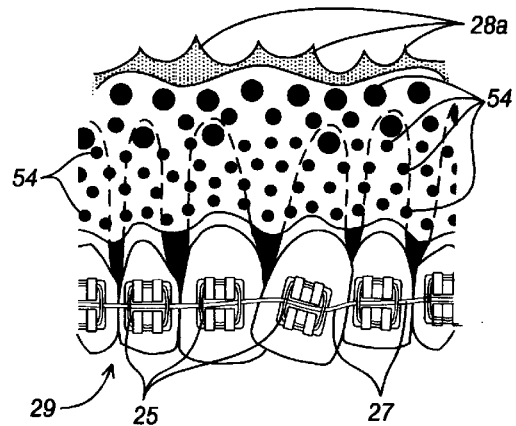
FIG. 17 shows upper anterior teeth with full-thickness gingival flaps reflected and exposed cortical plate partially decorticated solely with perforations.

The cortical plate 20 can also be sufficiently activated for the orthodontic method of this invention solely through the use of perforations, if desired, as shown in FIG. 17. Here again, where only perforations 54 are used to activate the cortical plate 20 the perforations are still placed in the cortical plate 20, as shown in FIG. 17, in the same manner as the perforations 54 shown in FIG. 14.

The use of either or both of these types of decortication has been found to be sufficient to cause bleeding points from the cortical bone 20 and the medullary bone 22 to create capillary pathways through which pluripotential cells migrate into the overlaying grafting material, when it is applied as described below, and to sufficiently trigger the regional accelerated phenomenon. The migration and activity of pluripotential cells and the regional accelerated phenomenon are well known in dental literature. See by way of example the article by Avinoam Yaffe, et al. entitled "Regional Acceleration Phenomenon in the Mandible Following Mucoperiosteal Flap Surgery" published in *Journal Periodontal*, January 1994, at pp. 79–83. See, by way of example, a study by Hwai-Nan Chang, et al., entitled "Angiogenic Induction and Cell Migration in an Orthopedically Expanded Maxillary Suture in the Rat", published in *Archives of Oral Biology*, volume 41, No. 10, 1996, pp. 985–96. Also see, by way of example, a literature review by Darwin J. Prockop entitled "Marrow Stromal Cells as Stem Cells for Nonhematopoietic Tissues," published in *Science*, volume 276, No. 4, April 1997, pp. 71–4. It was notable that the abutment teeth around which full thickness gingival flaps alone were used did not demonstrate any significant accelerated movement. But the other teeth around which both full thickness gingival flaps and partial decorticating were performed did show accelerated movement.

Figure 18:
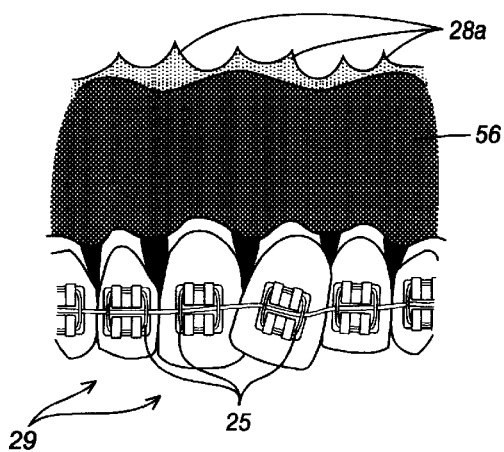
FIG. 18 shows upper anterior teeth with grafting material spread over partially decorticated cortical plates.
Figure 19:
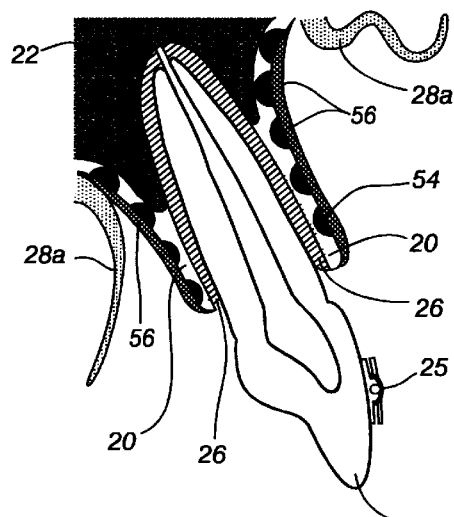
FIG. 19 is a cross section of an upper anterior tooth with grafting material spread partially decorticated cortical plate both facially and lingually.

Referring to FIGS. 18 and 19, grafting material 56 is then spread over the partially decorticated cortical plates 20. In the preferred orthodontic method of this invention bone grafting material is soaked in an antibiotic solution for at least 15 minutes. As much of the solution as possible is expressed from the bone grafting material. The bone grafting material is then spread over the partially decorticated cortical plates in a manner which attempts to achieve a fairly uniform layer of grafting material on the plates which is on average approximately one and one-half millimeters to two millimeters in depth. Excessive bone grafting material should be avoided, since it compromises the repositioning and suturing of the full thickness gingival flaps.

Among the grafting materials which can be used in accordance with this invention is BIO-OSS® chemically deproteinized protein bovine bone sold by Osetohealth Company of Shirley, N.Y.; Osteograf®/N-300 heat deproteinated bovine bone sold by CeraMed Corporation of Lakewood, Colo.; demineralized freeze-dried bone allograft ("DFDBA") which is human bone, chemically treated with alcohol to kill pathogens, which supposedly includes BMP's to stimulate bone formation and is available through many tissue banks; PerioGlass® synthetic bone grafting material available from Block Drug Corporation of Jersey City, N.J.; Biogran™ which is a synthetic bone grafting material available from Orthovita, Inc. of Malvern, Pa.; and BMP's being synthesized. Chemotactic attracting agents such as peptides which "call cells" to an area also have a potential place in this method by invention. These agents do not in themselves make the new bone, but attract cells to the area which lead to new bone formation One preferred bone grafting material used successfully in the method of this invention is a mixture by volume of two parts of DFDBA and one part of Osteograf®/N-300. For a discussion of bone grafting materials used in dentistry see the article by Carl E. Misch, et al. entitled "Bone-Grafting Materials in Inplant Dentistry", published in *Inplant Dentistry*, Volume II, No. 3 at pp. 158–67 and an article by Yorchiro Shigeyama, et al. entitled "Commercially-Prepared Allograft material Has Biological Activity in Vitro" published in *Journal Periodontal*, June 1995 at pp. 478–87.

Figure 20:
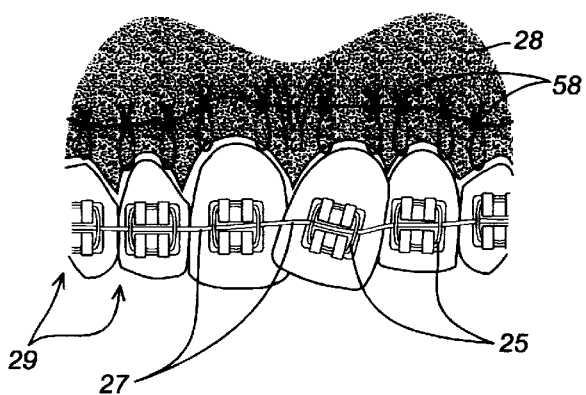
FIG. 20 shows upper anterior teeth post surgery with gingival flaps sutured.
Figure 21:
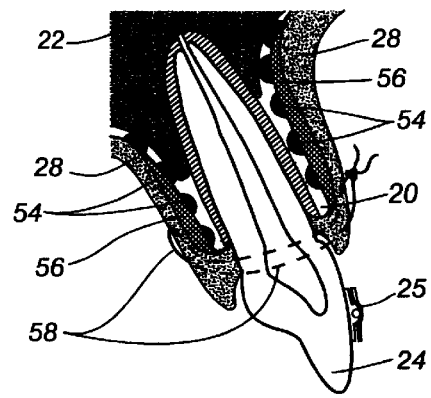
FIG. 21 is a cross section of an upper anterior tooth post surgery with its gingival flaps sutured.

The fall thickness gingival flaps 28a are replaced in their original positions and then, if possible, repositioned somewhat coronally using interrupted loop nonresorbable suture material such as 3-0 silk or Gore-tex® 58, as shown in FIGS. 20 and 21. Care must be taken to maintain the integrity of the layers of grafting material 56 during suturing, and the layers of grafting material may need to be smoothed as the suturing progresses. One or two silk (or Gore-tex®) sutures 58 can be used in each interdental area to orient the gingival flaps 28 properly. Fairly large bites of the attached gingiva 28 are taken with the suture needle. The sutures are drawn lateral to the center line of each interdental papilla, leaving the tips of the interdental papillae free to be pulled coronally. Approximately two millimeters of the flaps at the margins and coronal to the alveolar crest are cleared of the grafting material to aid in the readaptation of the gingiva to the cervical areas. So as not to jeopardize the slight coronal repositioning of the flaps, no periodontal dressing is used.

The patient is asked to only eat very soft foods and not do any sucking, such as by using a straw, for the next 10 days following surgery. The patient is administered 250 mg of penicillin 4 times daily for the next 10 days or 250 mg of Augmentin three times a day for the next 10 days. For discomfort the patient can be given Acetaminophen with Codeine 4 times daily and Naproxen Sodium 3 times daily as needed.

The sutures can be removed 12–14 days after the surgery, at the discretion of the clinician. During the active tooth movement, the patient should be checked at least once a month by the periodontist.

Retraction

The basic principles of the orthodontic method of this invention are applicable in retraction cases just as they are in expansion cases. In point of fact many retraction cases also require that teeth be expanded, as well, as indicated above. Additionally, since retraction cases normally require the extraction of teeth and move teeth in the opposite direction from the movement of teeth in expansion cases, retraction cases are handled somewhat differently.

First of all, in retraction cases the practitioners must conduct the same patient evaluation, including the same orthodontic and periodontal examinations and analyses used for expansion cases, to determine whether the orthodontic method of this invention should be used with respect to a particular patient. Additionally, an orthodontist and a periodontist or oral surgeon should collaborate to determine the teeth to be extracted, the teeth to be moved and the teeth to be used as anchors and where and how the cortical plates should be partially decorticated.

Figure 22:
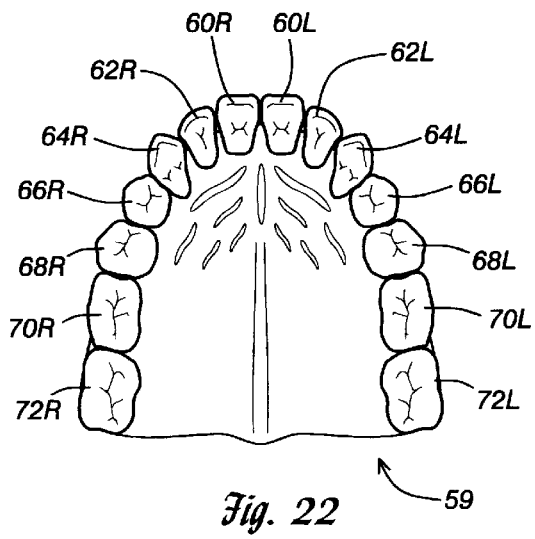
FIG. 22 is an upper dental arch requiring anterior teeth to be moved.
Figure 24:
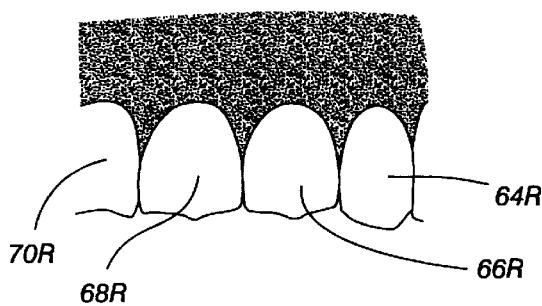
FIG. 24 is a partial side view of the dental arch shown in FIG. 22.

FIG. 22 shows an upper dental arch 59 of a patient requiring that an anterior segment of teeth be moved back to properly match the lower teeth. The upper dental arch 59 comprises a left central incisor 60L and a right central incisor 60R, a left lateral incisor 62L and a right lateral incisor 62R, a left canine tooth, or eye tooth, 64L and a right canine tooth 64R, a left first bicuspid 66L and a right first bicuspid 66R, a left second bicuspid 68L and a right second bicuspid 68R, a left first molar 70L and a right first molar 70R, and a left second molar 72L and a right second molar 72R. Assume, in a somewhat oversimplified example, that the patient has "buck teeth" which must be corrected and the significant problem is that the upper, central incisors 60L and 60R front teeth stick out too far. FIG. 24 is a partial sideview of the dental arch 59 shown in FIG. 22 which depicts the right first molar 70R, the right second bicuspid 68R, the right first bicuspid 66R and the right canine tooth 64R.

Figure 23:
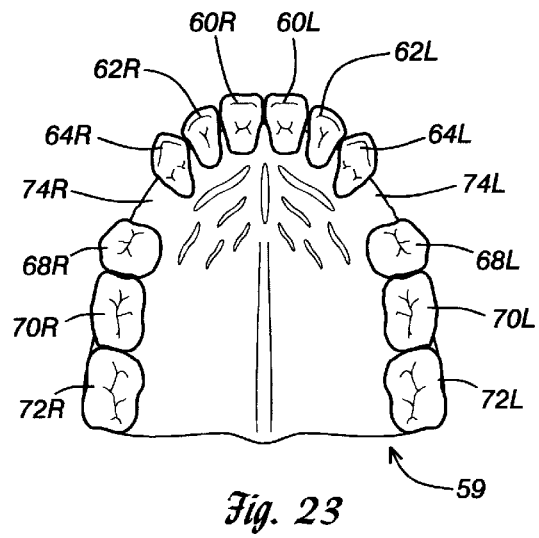
FIG. 23 is the upper dental arch of FIG. 22 after its first bicuspids have been removed.
Figure 25:
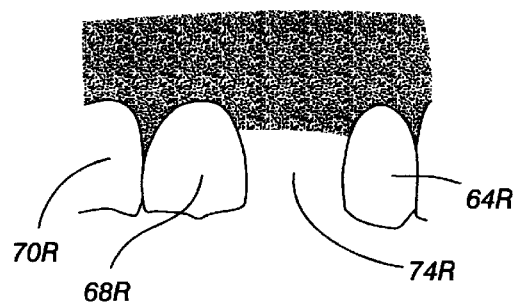
FIG. 25 is a partial side view of the dental arch of FIG. 23 showing the edentulous area where the right first bicuspid was removed.

As shown in FIG. 23, the right first bicuspid 66R and the left first bicuspid 66L are removed from the upper dental arch 59. This leaves the edentulous or extraction area 74L, between the canine tooth 64L and the second bicuspid 68L, and the edentulous area 74R, between the canine tooth 64R and the second bicuspid 68R. The edentulous areas 74L and 74R make room for the retraction of the anterior teeth comprising central incisors 60R and 60L, the lateral incisors 62R and 62L and the canine teeth 64R and 64L toward the second bicuspids 68L and 68R. These bicuspids are included in the posterior teeth which further include first molars 70R and 70L and second molars 72R and 72L. FIG. 25 is the same partial sideview shown in FIG. 24, except the first bicuspid 66R removed, leaving the extraction area 74R.

Figure 26:
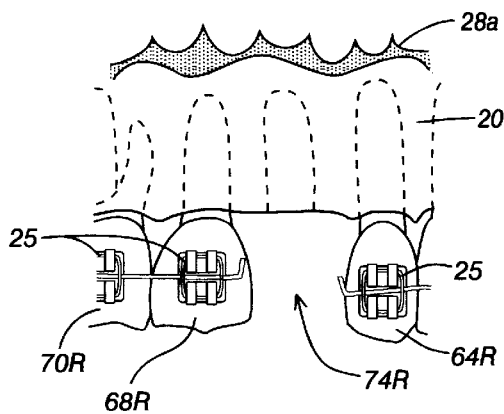
FIG. 26 shows the partial dental arch of FIG. 25 with brackets added to the teeth and full thickness gingival flaps reflected.
Figure 32:
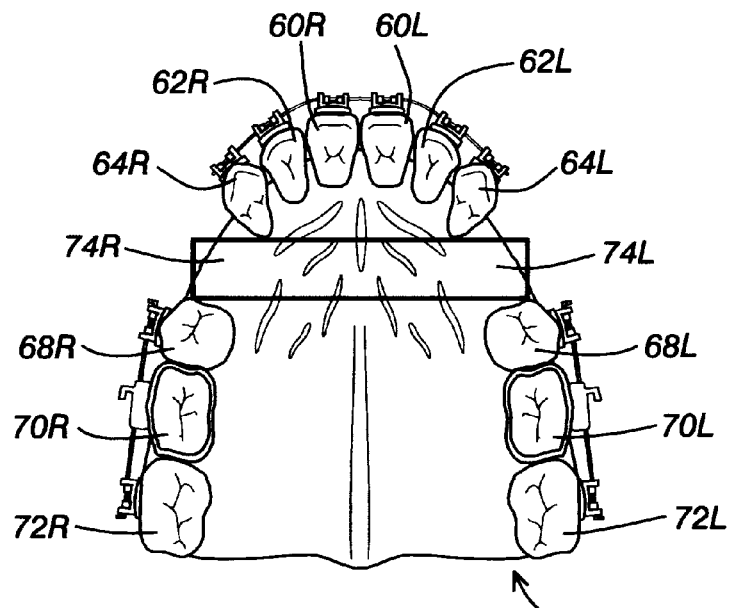
FIG. 32 is an upper dental arch with edentulous areas between the canine teeth and the second bicuspids.

The application of this invention to a retraction case following the removal of teeth is described in accordance with one preferred embodiment by referring to FIG. 26. After the first bicuspids 66L and 66R have been removed, and prior to the surgical procedures required in accordance with this invention, orthodontic appliances 25 can be installed on the anterior teeth 60R, 60L, 62R, 62L, 64R and 64L as shown in FIG. 32. The anterior right canine tooth 64R is also shown in FIG. 26. Orthodontic appliances 25 can also be installed at this time or the patient's posterior teeth 68R, 68L, 70R, 70L, 72R and 72L as also shown in FIG. 32. The anterior right second bicuspid 68R and right first molar 70R are also shown in FIG. 26. However, as indicated above, in retraction cases orthodontic appliances can be installed as late as approximately two to three weeks post-surgery.

Referring to FIG. 26, full thickness gingival flaps 28A are reflected both facially and lingually to gain access to the bone around the teeth to be moved. These same procedures are used for reflecting the gingival flaps for retraction cases as were used for expansion cases as explained above.

Figure 27:
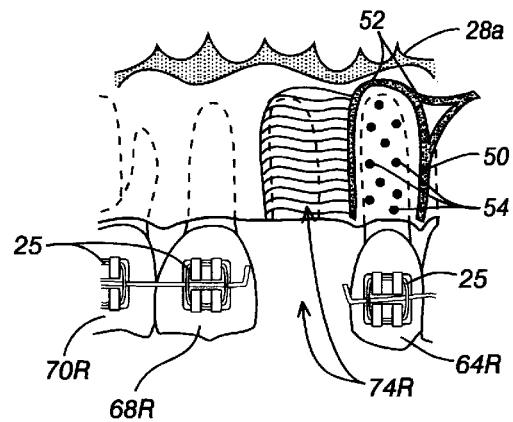
FIG. 27 shows the partial dental arch of FIG. 26 following a vertical osteotomy of the edentulous area and partial decortication of anterior teeth.

After the full thickness gingival flaps have been reflected, the exposed cortical bone overlaying the roots of the teeth to be moved, that is the anterior teeth, is partially decorticated both facially and lingually in the same manner described above for expansion cases. As shown in FIG. 27, partial decortication can be accomplished through the use of vertical grooves 50, horizontal grooves 52 between the vertical grooves 50 and/or perforations 54, as deemed appropriate by the practitioners performing the procedure.

Additionally, in further accordance with this invention a vertical osteotomy was performed in the edentulous area 74R, between the right canine tooth 64R and the right second bicuspid 68R where the roots of the upper first bicuspid 66R had been located prior to its extraction. A thin layer of medullary bone should be retained over the root surfaces of the right canine tooth 64R and the right second bicuspid 68R adjacent to the osteotomy site. This site is illustrated by the wavy lined portion of the edentulous area 74R shown on FIG. 27. A similar vertical osteotomy is performed in the edentulous area 74L shown in FIG. 23, between the left canine tooth 64L and the left second bicuspid 68L.

Figure 30:
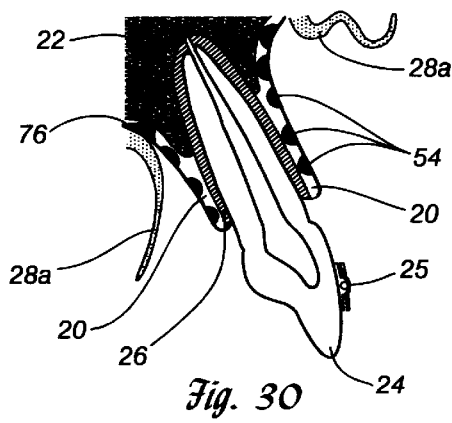
FIG. 30 is a cross section of an upper anterior tooth having partially decorticated cortical plate.

The corticotomy for retraction cases may include a wedge-shaped groove 76 placed lingually or inside the upper front teeth and extending to include the entirety of the extraction sites as shown in FIG. 30. This horizontal wedge-shaped groove 76 serves as the pivotal area from which the anterior segment of bone tips back, which we call osteogenic retraction.

Figure 28:
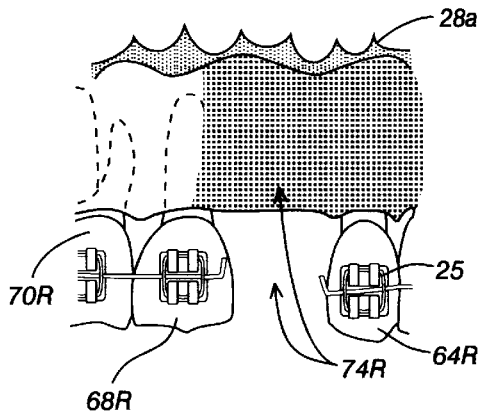
FIG. 28 shows the partial dental arch of FIG. 27 with grafting material spread over partially decorticated cortical plate.

As shown in FIG. 28 a thin layer of grafting material is spread over the partially decorticated cortical plate 20 in the same manner used in expansion cases, as described above. In addition, the osteotimized sites 74R and 74L are loosely filled with the same grafting material.

Figure 29:
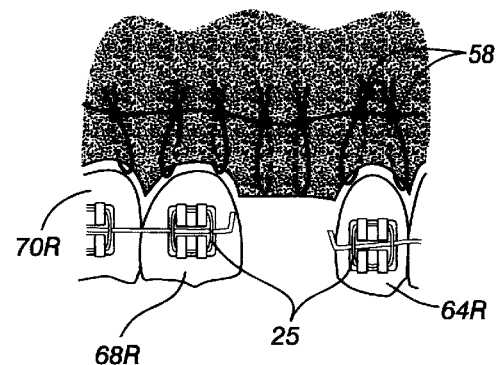
FIG. 29 shows the partial dental arch of FIG. 28 post surgery with the gingival flaps sutured.
Figure 31:
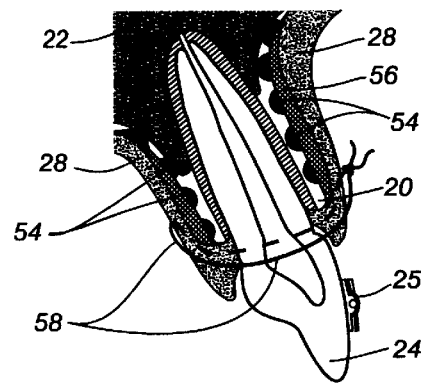
FIG. 31 is a cross section of an upper anterior tooth post surgery with its gingival flaps sutured.

The gingival flaps are then replaced to their original positions and over the bone grafting material, using sutures to hold them in place in the same manner as in expansion cases. This is depicted in FIGS. 29 and 31. Approximately two weeks after surgery sutures can be removed. A short time thereafter one or more orthopedic retraction devices can be installed in the patient's dental arch which is undergoing retraction.

Figure 33:
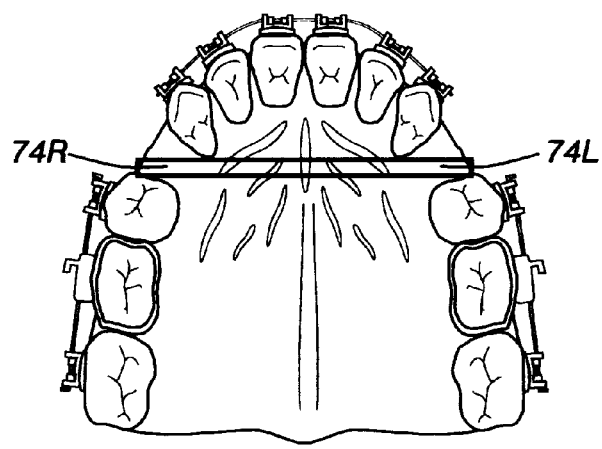
FIG. 33 is the upper dental arch of FIG. 32 after retraction according one aspect to this invention.

FIG. 32 shows the upper dental arch 59 prior to the time when retraction is begun. FIG. 33 shows the upper dental arch after retraction has been completed. Orthopedic forces are used to retract the anterior teeth of the dental arch 59 as shown in FIG. 32, into the edentulous areas 74R and 74L, as shown in FIG. 33. Due to the application of orthopedic forces major retraction movements can be completed within approximately four to six weeks time.

Orthopedic forces can be applied to move the anterior teeth and the segment of bone that surrounds them in any manner which is found to be expedient.

Figure 34:
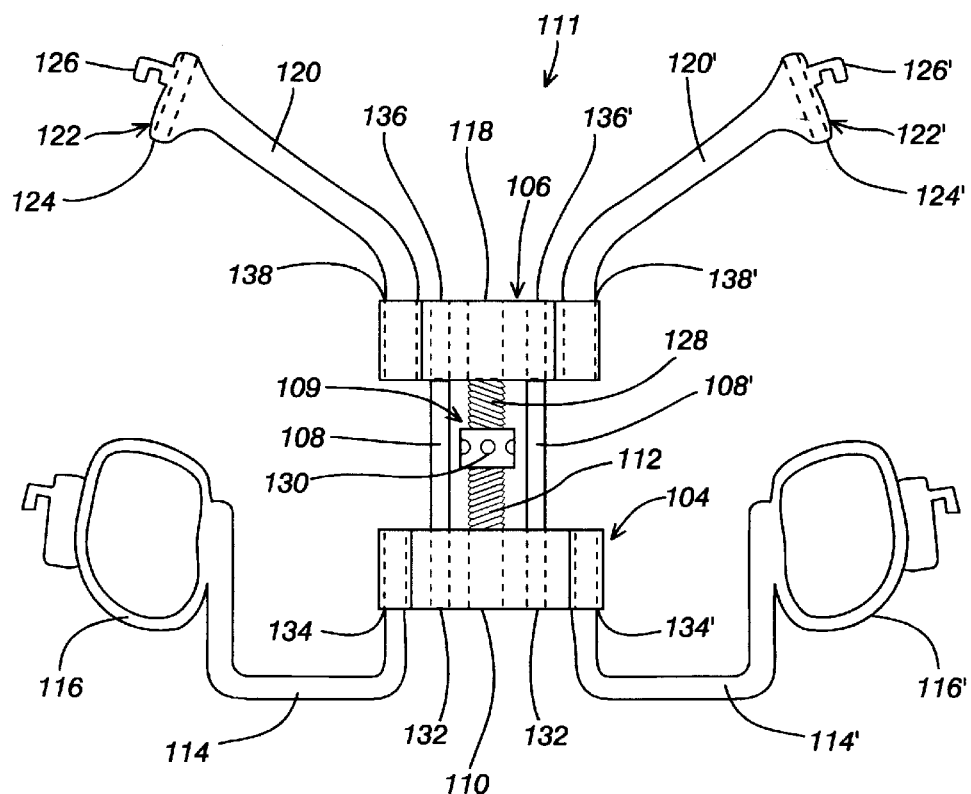
FIG. 34 is a top view of a retraction device made in accordance with one aspect of this invention.

Referring to FIG. 34, a retraction device 111 is used to apply orthopedic forces across the edentulous areas 74R and 74L. The retraction device 111 comprises a back body 104, a front body 106, and a screw member 109 operatively connected between the back body 104 and the front body 106. The screw member 109 is adjustable to cause the back body 104 and the front body 106 to move away from one another. It can also cause them to move toward one another while developing an orthopedic force between them and between anterior teeth and posterior teeth.

The retraction device of this invention further includes at least one slide rod between its front body and its back body. The retraction device 111 includes two slide rods 108, one on each side of the screw member 109. The screw member 109 has a first section 112 having screw threads formed in one direction arid a second section 128 having screw threads formed in the opposite direction. An adjuster block 130 is located between the two sections 112 and 128 of the screw member 109.

The back body 104 has a hole 110 having screw threads cut within it to receive the section 112 of the screw member 109. The front body 106 has a hole 118 in it which has screw threads to receive the section 128 of the screw member 109. The sections 112 and 128 of the screw member 109 are attached to opposite sides of an adjuster block 130. The adjuster block 130 has four holes in it. These holes allow an adjustment key to be placed in them by a dentist or a patient to adjust a level of force to be applied between the posterior teeth and the anterior teeth. The screw sections 112 and 128 are threaded in opposite directions so that as they turn with the rotation of the adjuster block 130, the back body 104 and front body 106 are drawn toward one another or away from one another depending on the direction in which the screw 109 is turned.

The retraction device of this invention includes at least one slide rod extending between its back body and its front body. The retraction device 111 includes a pair of slide rods 108 which can slide through the pair of holes 136 in the front body 106 and a pair of holes 132 in back body 104.

In accordance with this invention, a retraction device is constructed so as to enable its front body to be coupled to at least one anterior tooth and to enable its back body to be coupled to at least one posterior tooth. The retraction device can then transmit an orthopedic force between these teeth as the screw member is adjusted to move the anterior teeth. In the embodiment of this invention shown in FIG. 34, the back body 104 has arms 114 and 114' attached to it. Arm 114 can be connected to at least one of the posterior teeth on the right side of the upper dental arch 59, while arm the 114' can be attached to at least one of the posterior teeth on the left side of the dental arch 59. The back body 104 has two holes 134 and 134' which accept the arms 114 and 114'. In the illustrated embodiment the arms 114 and 114' are attached to a first molar band 116 and a first molar band 116', respectively, which can be cemented to first molars in the upper right posterior and upper left posterior portions of a patient's dental arch.

Figure 36:
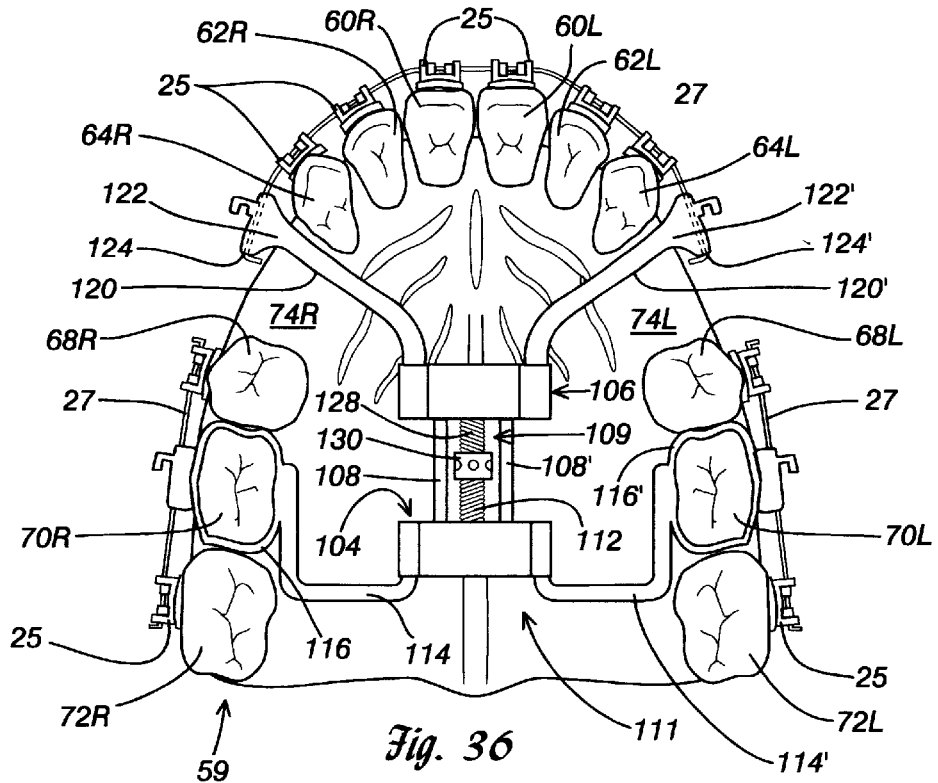
FIG. 36 is an upper dental arch in which the retraction device of FIG. 34 is installed.

Similarly, the front body 106 has a pair of arms 120 and 120' which are adapted to be connected to at least one anterior tooth on the right side and left side, respectively, of a patient's upper dental arch. The front body 106 has two holes 138 and 138' which are sized to accept the wire arms 120 and 120'. The wire arms 120 and 120' extend forward, as shown in FIG. 36, so as to approximate the brackets 25 of the canine teeth 64R and 64L. The ends of the wire arms 120 and 120' are fit with an attachment apparatus 122 and 122', respectively. The attachment apparatus 122 and 122' include holes 124 and 124' which can receive ligature wires or archwires 127 attached to a patient's teeth. They also include hooks 126 and 126' for the attachment of ligature wires, springs or other auxiliary items useful in the performance of the orthodontic method of this invention.

FIG. 36 is a front elevation of the front body 106 which also includes the arms 114 and 114' and the arms 120 and 120'. It shows the contour of the front body 106 and the placement of the screw half 128, the slide rods 108 and the arms 120 and 120' within the front body 106. The front elevation of the back body 104 would be substantially identical to that of the front body 106, except the arms 114 and 114' are substituted for the arms 120 and 120'.

Although the illustrated embodiment of the orthodontic device 111 uses round wire arms 114, 114' 120 and 120', these arms may be constructed of any shape acceptable to those skilled in the art and can be made of any material which is desired. The wire arms 114 and 114' and the wire arms 120 and 120' may be attached to the posterior and anterior teeth, respectively, through the use of any attachment apparatus which is convenient to those skilled in the art.

FIG. 36 shows the dental arch 59 with the retraction device 111 in place. The brackets 25 and archwire 27 have been installed in the manner indicated above. The back body 104 is connected through the wire arms 114 and 114' and the first molar bands 116 and 116' to the upper first molars 70R and 70L in the posterior section of the dental arch 59. The front block 106 is connected through the wire arms 120 and 120' and the holes 124 and 124' in the attachment apparatus 122 and 122' to the anterior teeth of the dental arch 59. FIG. 36 shows the archwire 27 passing through the holes 124 and 124' to fasten the anterior teeth to the wire arms 120 and 120'. However, retraction can be accomplished without the use of the archwire 27 by attaching the arms 120 and 120' to the canine teeth 64R and 64L. Even without the use of the archwire 27, all of the anterior teeth can be retracted upon the retraction of the canine teeth 64R and 64L through the use of the retractor device 111 of this invention.

Based on our studies to date, the retraction device 111 primarily moves the anterior teeth 60R, 60L, 62R, 62L, 64R and 64L, the partially decorticated cortical bone adjacent these teeth and the other supporting bone surrounding these teeth into the edentulous areas 74R and 74L. No more than a slight movement of the posterior teeth occurs since the cortical bone adjacent these teeth was not partially decorticated and thus was not activated.

If desirable, one or more posterior teeth could also be moved toward the edentulous areas 74R and 74L in the same manner the anterior teeth are moved. That is, the cortical bone adjacent these teeth that are to be moved can be partially decorticated, as explained above, starting with the second bicuspids 68R and 68L. Then bone grafting material would be placed between the cortical bone and adjacent gingival flaps and the gingival flaps sutured as necessary.

The use of the wire arms 120 and 120' to retract the anterior teeth results in small edentulous areas, approximately the size of the diameter or width of the wire arms 120 and 120', when retraction in accordance with the principles of this invention is completed. These edentulous areas are located between the canine tooth 64R and the second molar 68R and the canine tooth 64L and the second molar 68L as shown in FIG. 33. The anterior teeth must be retracted into these remaining spaces using conventional orthodontic methods and devices.

Figure 35:
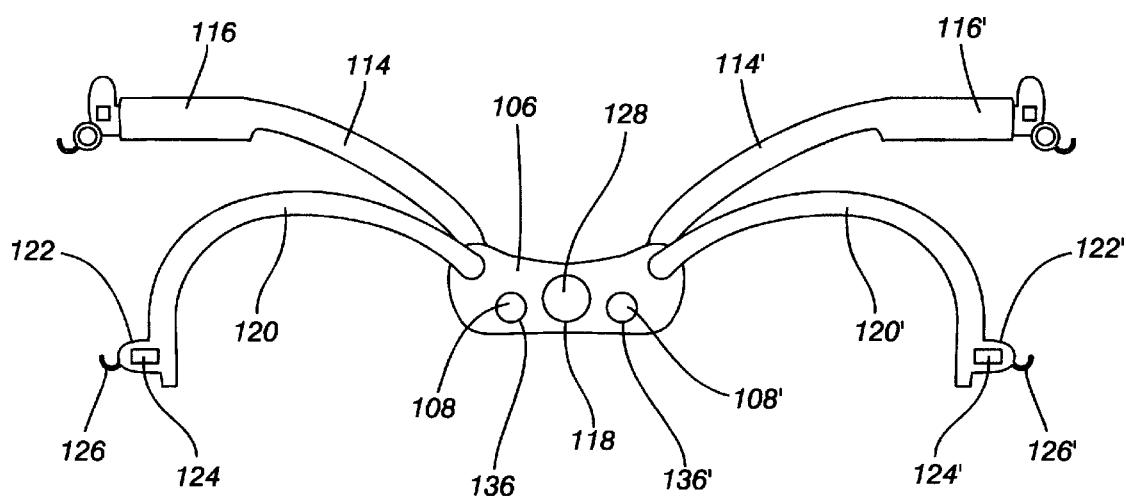
FIG. 35 is a front view of the retraction device of FIG. 34.
Figure 37:
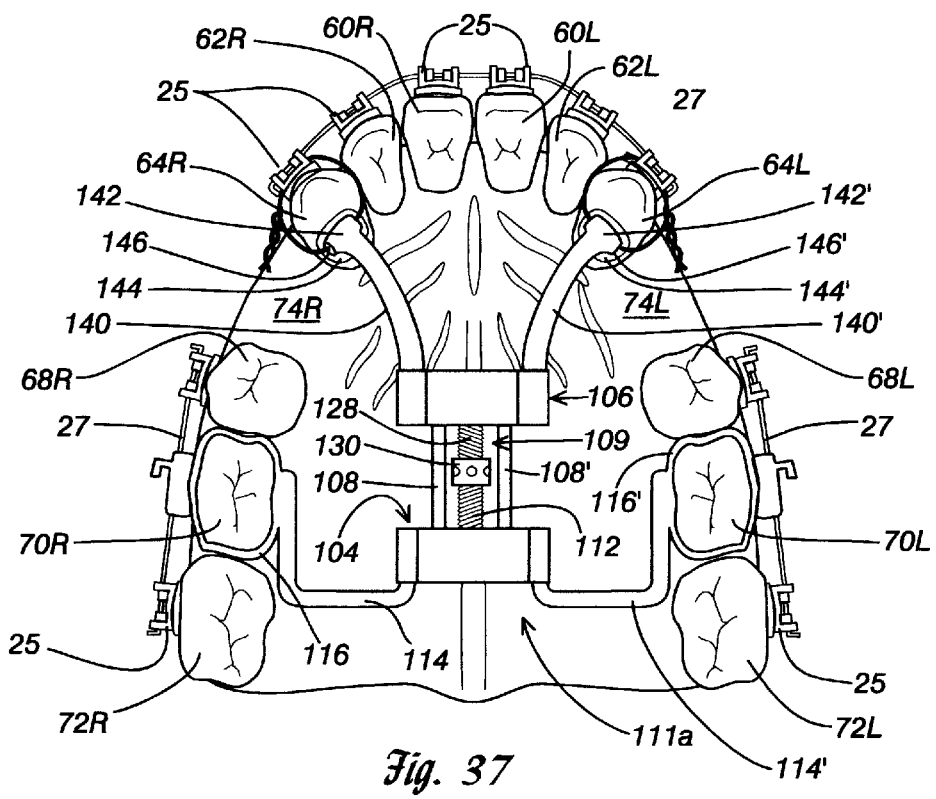
FIG. 37 is an upper dental arch in which is installed another retraction device made according to this invention.

FIG. 37 shows another embodiment of a retraction device 111a installed in the dental arch 59. In this configuration the wire arms 120 and 120', shown on retraction device 111, in FIGS. 34–36, are replaced by wire arms 140 and 140' which are also attached to the front body 106 of the retraction device 111a. The wire arms 140 and 140' extend forward so that they approximate the lingual aspect of the canine teeth 64R and 64L. The wire arms 140 and 140' are fitted with attachment apparatus 142 and 142'. The attachment apparatus 142 and 142' each includes a surface 144 and 144', respectively, which can be bonded to the lingual surfaces of the canine teeth 64R and 64L. The apparatus 142 and 142' also include holes 146 and 146' through which ligature wires or archwires can be inserted and tied to or engaged with the canine teeth 64R and 64L. The attachment apparatus 142 and 142' may also include hooks and other means for attaching ligature wires, springs and other auxiliary devices used in orthodontics.

Another means for applying orthopedic forces in accordance with this invention is a retraction device 80 which is shown in FIG. 38. The retraction device 80 comprises a back body 82, a front body 84, a screw member 93 operatively connected to the back body 82 and the front body 84, and a single slide rod 88 extending between the back body 82 and the front body 84. The back body 82 has a hole 86 of such a size that it can accept a slide rod 88 in it. It also has a hole 90 which is threaded to accept one section 92 of a threaded screw member 93. The back body 82 also has a third hole 94 which can be used to tie ligature wires, springs and other possible auxiliary devices to the retraction device 80. In place of the hole 94 items such as hooks, cleats, buttons and other connectors could be added to the retraction device 80 to connect it to teeth or braces. A side view of the back body 82 is shown in FIG. 39.

The front body 84 has a hole 96 which is a size to accept the slide rod 88. It also includes a threaded hole 98 which accepts a second section 100 of the threaded screw member 92. The front body 84 further includes the hole 101, similar to hole 94, which is adapted to have ligature wires 99, or springs or other auxiliary devices to it to be attached to one or more anterior teeth as shown in FIG. 41.

The side rod 88 is welded or otherwise attached to the back body 82, whereas it can slide through the hole 96 in the front body 84. The thread screw halves 92 and 100 are threaded in the opposite directions so that as they turn the back body and front body are drawn toward one another or away from one another, depending on the direction of rotation of the screw number 93. The screw member 93 has an adjuster block 103 with four holes in it between the screw sections 92 and 100. The holes in adjuster block 103 also allow a key to be placed in them by a dentist or a patient to adjust the level of forces to be applied.

The retraction device 80 further includes an anti-rotation stop 95 which inhibits the rotation of the retraction device 80 when the screw member 93 is rotated to apply force between a patient's posterior teeth and anterior teeth. In the preferred embodiment the anti-rotation stop 95 is a hook attached to the back body 82. The anti-rotation stop can also be a straight extension or another shape other than a hook.

Alternatively, an anti-rotation stop can be installed on the front body 834 rather than on the back body 82, or in addition to installing it on the back body 82. It should, however, be positioned to inhibit rotation of the retraction device 80 when the adjuster block 103 is rotated to decrease the distance be-ween the back body 82 and the front body 84.

FIG. 40 shows a section of a dental arch which is adapted to have a retractor device 80 placed on it. The brackets 25 and arch wire 27 have been installed in the manner indicated above. Additionally, a band 105 has been installed on the first right molar 70R. A tube 107 has been soldered or welded to the band 105 prior to installation. The tube 107 is of a size such that it can receive the slide rod 88 of the retractor screw 80. FIG. 41 shows how the slide rod 88 of the retractor screw 80 fits through the tube 107. As a result, the back body 82 is coupled to the right first molar 70R when force is exerted in an anterior direction on the retraction device 80.

After installation, ligature wires 99 can be installed and, if desired, woven in a figure eight about the brackets 25 of one or more of the anterior teeth as shown in FIG. 41. A similar retractor screw, having the pitch of the halves of its screw threads reversed, can be installed on the left hand side of the dental arch in the same manner. Ligature wires on that retractor screw would then be woven about the brackets 25 of at least one of the left anterior teeth so as to enable orthopedic forces to be applied on both sides of the dental arch.

Figure 4:
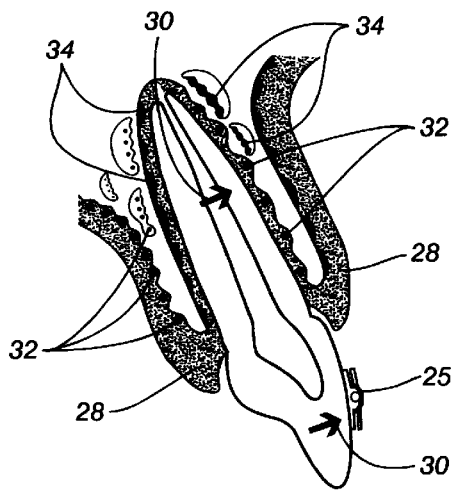
FIG. 4 is a cross section of an upper anterior tooth showing cortical plates remodeled during orthodontic treatment.
Figure 5:
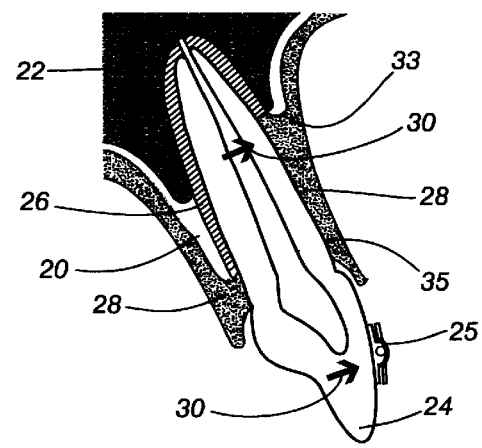
FIG. 5 is a cross section of an upper anterior tooth showing dehiscence formation resulting from orthodontic treatment.
Figure 6:
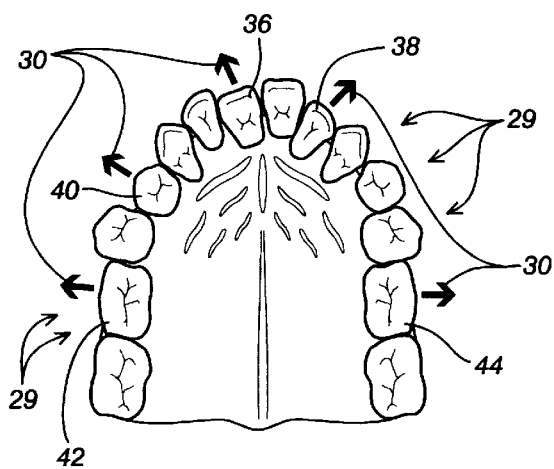
FIG. 6 is an upper dental arch having overlapped and crowded teeth.
Figure 7:
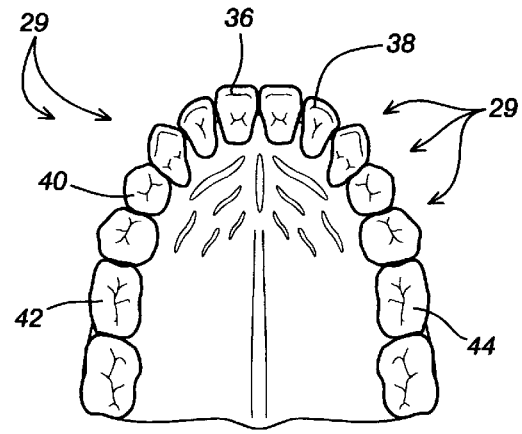
FIG. 7 is the upper dental arch of FIG. 6 after the teeth have been straightened.
Figure 8:
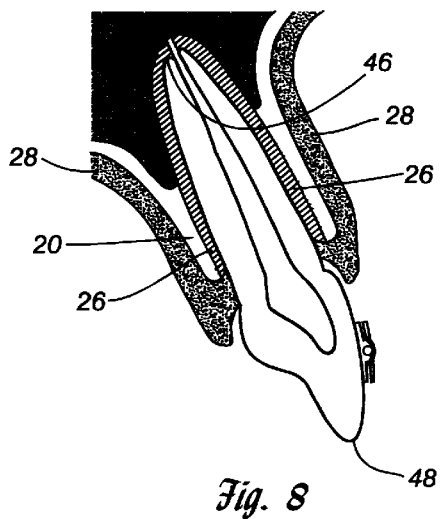
FIG. 8 is a cross section of a single rooted tooth prior to orthodontic treatment.
Figure 9:
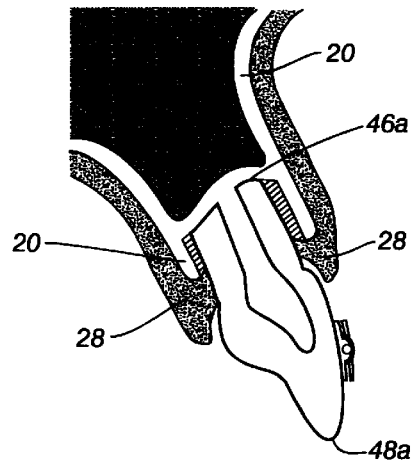
FIG. 9 is a cross section of a single rooted tooth which reportedly had root resorption after orthodontic treatment.

The retraction devices of this invention may be constructed out of components and materials used by those skilled in the art to construct orthodontic palatal expansion devices such as shown in U.S. Pat. No. 4,347,054 Kraus et al., U.S. Pat. No. 4,354,832 Wallshein, U.S. Pat. No. 4,433, 956 Witzig, U.S. Pat. No. 4,482,318 Förster, U.S. Pat. No. 5,281,133 Farzin-Nia, U.S. Pat. No. 5,002,485 Aagesen, U.S. Pat. No. 5,439,377 Milanovich, and U.S. Pat. No. 5,472,344 Binder et al. U.S. Pat. No. 4,483,674 Schutz discloses different types of orthodontic tooth regulating devices, including a retraction device which is shown in FIG. 4 of that patent. However, due to the apparent light structure of the retraction device shown in FIG. 4, it does not appear that this device can apply an orthopedic force to the teeth being retracted.

The design and nature of fixed rapid palatal expanders are discussed in a book by Anthony Viazis entitled *Atlas of Orthodontics: Principles and Clinical Applications*, published by W. B. Saunders Company, pp. 205–13, 1993; and in a book by James A. McNamara, et al., entitled *Orthodontic and Orthopedic Treatment in the Mixed Dentition*, published by Needham Press, pp. 131–44, 1993.

The design and nature of removable expanders are addressed in a book by T. D. Foster entitled *A Textbook of Orthodontic*, published by Blackwell Scientific Publications, 2nd Edition, pp. 246–61, 1982; and in a book by William R. Proffit, et al., entitled *Contemporary Orthodontics*, published by The C. V. Mosby Company, pp. 272–86.

Movement processes related to the configuration of palatal expanders are addressed in a study by Chester S. Handelman entitled "Nonsurgical Rapid Maxillary Alveolar Expansion in Adults: A Clinical Evaluation," published in *The Angle Orthodontic*, Vol. 67, No. 4, pp. 291–305, 1997; and a study by Samir E. Bishara, et al., entitled "Maxillary Expansion: Clinical Implications" published in *Am. J. Orthod. Dentofac, Orthop.*, Vol. 91, No. 1, pp. 3–14, 1987.

None of these expanders or physiological processes involves the same type of orthopedic movements that we are accomplishing with the retraction devices of this invention.

Conventional expansion screws start from a closed position in a side-to-side position in a patient's jaw. Upon adjustment, two or more sections of these screws are spread apart, which in turn widens or spreads apart teeth or jaws. The design of these expansion screws is not to pull teeth, sections of teeth, sections of jaws or jaws together as is required from the retraction devices of our invention.

The orthodontic method and retraction devices of this invention were proven to be effective in the following examples of treatment of patients:

EXAMPLE 1

A 38 year old female presented for treatment. An orthodontic evaluation revealed a Class 1 anterior crowded malocclusion. It was determined that this case would most appropriately be treated by expansion. A periodontal evaluation revealed a healthy periodontium with no signs of significant past damage that might compromise treatment. It was also determined that there were no other dental or medical conditions that would preclude treatment. Orthodontic appliances consisting of bands on the first molar, brackets on all of the other teeth, and upper and lower arch wires, were installed by the orthodontist. Three days following the activation of the orthodontic appliances the patient presented at the periodontal office for the surgical aspect of this invention. The patient had premedicated herself with 3 grams of Amoxicillin one hour prior to this appointment. The surgery was performed under intravenous sedation and local anesthesia. The surgery in both the upper and lower dental arches was completed at this one sitting. Even though it was only the six upper anterior teeth and the six lower anterior teeth that were targeted for the partial decorticating and resulting "bone activation", full thickness gingival or mucoperiosteal flaps were reflected both facially and lingually around all of the teeth. The reflection of the flaps was preceded by a sulcular or intracrevicular incision around all of the teeth. So as to jeopardize the blood supply to the flaps as little as possible, no vertical releasing incisions were used.

The "bone activation" was performed mostly in the manner of facial arid lingual corticotomy grooves around the six upper and six lower anterior teeth, utilizing a #2 round bur in a high speed handpiece under copious water irrigation. The vertical groves started just shy of the interdental crest and extended two to three millimeters beyond the apices of the teeth, where they were joined by a horizontal groove. Pin-point corticotomy perforations were made both facially and lingually to mark the approximate location of the apices of the teeth prior to performing the vertical and horizontal corticotomy grooves. The grafting material was then spread over the corticotomy preparations in the cortical plates both facially and lingually. In this case the grafting material consisted of two parts by volume of demineralized freeze-dried bone allograft powder and one part by volume of deproteinated bovine bone powder (Osteograf®/N-300). The grafting material was soaked for approximately fifteen minutes in a tetracycline solution (20 mg of Achromycin V per 1 cc of bacteriostatic water) prior to usage in the surgical sites. (In more recent cases we have discontinued the use of the tetracycline solution in favor of Clindamycin solution, 10 mg of Clindamycin Phosphate per 1 cc of sterile water). The mucoperiosteal flaps were then replaced to their original position and sutured with interrupted loop non-resorbable suture material, essentially having the effect of trapping the grafting material between the under surface of the mucoperiosteal flaps and the outer surface of the "activated" cortical plates. 3.0 black braided silk suture material was used in this case, but this material has more recently been abandoned in preference to Gore-tex® suture material. Six milligrams of Decadron was administered intravenously prior to dismissing the patient. Except for some facial swelling the healing was rather uneventful.

Subsequent to the surgical procedure, the patient was seen by the orthodontist approximately every 14 days for appliance adjustments. The major expansive orthodontic movements were complete at two months into the treatment and after three appliance adjustments had been performed. The finer finishing movements required 3 additional adjustment appointments to bring the case to completion. The orthodontic work was completed and the orthodontic appliances removed 99 days after placement, with a total of 6 adjustment appointments having been required. The patient was then placed in removable retainers.

A post-treatment periodontal evaluation indicated:
A) no significant gingival recession;
B) no significant interdental papillary shrinkage;
C) no pocket probing depths greater than 3 mm;
D) no loss of pulpal vitality;
E) no significant apical root resorption was evident through periapical radiographic evaluation; and
F) no loss of interproximal bone was evident through periapical radiographic evaluation.

An evaluation of lateral cephalometric radiographs indicated what appeared to be a layer of new bone on the facials of the roots of the upper and lower incisors. A post-treatment CT scan also indicated a continuous cortical plate with no significant dehiscence formation.

The only definitive manner in which to determine whether or not bone regeneration had actually taken place was through histologic evaluation requiring re-entry of the case to obtain bone biopsies. The bone biopsies were obtained approximately 9 months following the original grafting procedure under intravenous sedation and local anesthesia a full thickness flap was again reflected, but only on the facials of the lower teeth, to gain access to the roots of the 6 lower anterior teeth. Visual examination revealed what appeared to be a thick, continuous layer of cortical bone with a marbleized appearance. Several bone biopsies were secured, some of which extended to the root surfaces. The sites bled readily when the bony cuts were made. The bony defects which resulted were regrafted. On this occasion, the grafting material consisted of a 50/50 mixture by volume of Osteograf®/ N-300 and demineralized freeze dried bone allograft powder, which was first soaked in a 10 mg/ml Clindamycin solution. The full thickness gingival flap was returned to its presurgical position and sutured with 3.0 black braided silk interrupted loop sutures. The healing was again uneventful.

The bone biopsies were decalcified, stained with H and E, and then examined under non-polarized and polarized light. The examination revealed almost complete conversion of the grafting material into the patient's own bone. Only a few small fragments of the grafting material were found to not yet have completely resorbed, and these were located close to the outside surface of the newly developing layer of bone. The entire thickness of the bone biopsies, from the outside surface of the bone to the root surface, was newly developing bone. This indicated to us that if the bone grafting had not been performed, dehiscence formation would likely have resulted over the root surfaces in these areas, due to the expansion of the prominences of the roots outside the original limits of the alveolar bone. In one biopsy the new bone was 4.8 millimeters in thickness. By happenstance, the bone biopsy that was removed from the facial of #27 (lower right canine) included a small piece of attached root surface. The histologic evaluation of this specimen under non-polarized and polarized light revealed new bone attached to a piece of cementum on the root surface and a new periodontal ligament, indicating the formation of a new, healthy periodontium in this area.

A follow up evaluation revealed a healthy periodontium with no signs of any breakdown. Since we know that there is adequate bony support around the roots of the teeth, we anticipate that this case will remain stable long-term.

Prior to the use of grafting material in the manner relating to the method of invention, grafting involving the alveolar ridges and teeth with their supporting periodontium was generally undertaken in an attempt to regenerate alveolar bone which had been lost due to disease, atrophy, or trauma. The use of crafting materials by this method of invention is a unique application in that grafting is being performed in a healthy area to maintain and augment the health of the area.

EXAMPLE 2

A thirteen year old male presented for possible treatment. Orthodontic records were taken and it was determined that he suffered from a class II crowded malocclusion. Due to the crowding and incomplete eruption, the upper canines were positioned superiorly which produced an unsightly appearance. To straighten the teeth required major movements in the upper arch by retraction and major movements in the lower arch by expansion.

A periodontal evaluation indicated an absence of any significant disease and the presence of good bony support for the teeth. The upper and lower canines were positioned very prominently in the arches and facially exhibited a very thin zone of attached fibrotic gingiva. To lessen the possibility of encountering gingival recession in these areas during the course of the orthodontic treatment, the decision was made to increase the zone of attached gingiva by means of free gingival grafting. This required a surgical session, at which time free gingival grafts were harvested from the palate and grafted to the facials of the canines. This free gingival grafting would have had to have been performed regardless of whether the orthodontic work was to be done by this invention or by conventional means. The free gingival grafting was successful and the patient was referred back to the orthodontic office to begin the treatment by this invention.

Arrangements were made for the removal of the two upper first bicuspids. After the extraction sites had healed, bands were cemented on all four first molars and brackets were cemented on all of the other teeth. The upper four incisors were splinted together with a segment of arch wire, as were the teeth remaining in each side of the upper posterior area. The lower teeth were connected with an arch wire that was activated.

Due to scheduling conflicts, the patient was not able to return for the surgical portion of this invention for approximately one month. The surgery in both the upper and lower arches was completed at the same appointment and was carried out under intravenous sedation and local anesthesia. Facial and lingual full thickness flaps were reflected around all of the remaining upper and lower teeth. The partial decorticating of the exposed cortical plates was achieved with a combination of grooves and pin-point perforations that were performed booth facially and lingually around the six upper and lower anterior teeth. The groves consisted of interdental vertical cuts starting just shy of the interdental crest and extending 2 to 3 millimeters beyond the apices of the teeth. Horizontal cuts connected the vertical cuts beyond the apices of the teeth. The pin-point perforations were performed in the cortical plates overlaying the prominences of the roots. Additionally, a wide vertical osteotomy was performed between the canine and second bicuspid on each side of the upper arch where the roots of the upper first bicuspids had been located prior to the extraction of theses two teeth. A thin layer of medullary bone was retained over the root surfaces of the canines and second bicuspids adjacent to the osteotomy sites. A 50/50 mixture of heat deproteinated bovine bone powder (Osteograft®/N-300) and demineralized freeze dried bone allograft powder was then applied in a layer over the partially decorticated cortical plates both facially and lingually. An attempt was made to provide a fairly uniformed layer of grafting material at least two millimeters in thickness. The osteotomized sites were loosely filled with this same grafting mixture. The grafting mixture had first been soaked in a 20 mg/ml tetracycline solution for approximately 15 minutes. The excess fluid was expressed from the grafting mixture before usage. In more recent cases a 10 mg/ml Clindamycin solution has been substituted for the tetracycline solution.

The full thickness flaps were then returned to their original (pre-surgical) position which had the effect of trapping the grafting material between the underside of the mucoperiosteal flaps and the outside surface of the partially decorticated cortical plates. The flaps were then sutured in place with 3.0 black braided silk suture material in the manner of interrupted loop suturing. In more recent cases the silk suture material has been abandoned in favor of Gortex® suture material.

The patient reported no significant post-operative discomfort and did not find it necessary to take any of the pain medication that was prescribed for him. The sutures were removed 14 days after the surgery. Two weeks later the orthopedic retraction devise was installed in the patient's upper arch. The patient was instructed in the manner in which to adjust the appliance on a daily basis. After 21 days the major retraction movements were completed and the orthopedic retraction devise was removed. By this time the major expansion movements had also been completed in the lower arch. The remainder of the orthodontic treatment consisted of completing the finer finishing movements. The case was de-bracketed approximately 7 months following the surgery and 8 months following the bracketing, with a total of 13 adjustment appointments having been required.

A post-treatment evaluation indicated no periodontal breakdown. A comparison of the pre-treatment and post-treatment periapical radiographs did not find any significant apical root resorption. A rather well defined layer of what appeared to be new bone could be seen over the outside (facial) prominences of upper and lower incisors by lateral cephalometric analysis. An analysis of the pre-treatment and post-treatment CT scans revealed continuous cortical plates, no significant dehiscence formation over the prominences of the roots and no residual indentations in the alveolar ridge in the osteotomized sites. With good bone support for the teeth in their completed positioning, we anticipate a stable long-term result.

The use of orthopedic forces, as demonstrated in this case dramatically increases the rate of the retraction. With orthopedic forces, retraction cases can now be completed on a routine basis in 6 to 8 months. Since the initiation of the use of orthopedic forces, we have not found any significant apical root resorption in the retracted teeth. This is most likely attributable to the reduction in treatment time. Lateral cephalometric analysis shows that we are also getting some displacement of the dentoalveolar unit created by the combined osteotomies and corticotomies. This is the type of situation that Suya assumed was occurring with the dentoalveolar units created by pure corticotomies in expansion cases, but which we have shown is not the case. The use of the grafting has also eliminated the deep indentations in the alveolar ridge in the osteotomized extraction sites.

EXAMPLE 3

A 23 year old male presented for an orthodontic evaluation. One year earlier he had been treated for generalized incipient to moderate periodontitis. This was treated non-surgically by means of a series of deep scalings and root planings that were performed by quadrant under local anesthesia. This treatment also included the use of two 2 week regimes of Doxycycline 100 mg/day. The patient's oral hygiene improved marginally and most of the periodontal pocketing resolved leaving no probing depths greater than 3 millimeters. Upon returning for the orthodontic evaluation one year later, he indicated that the third molars and supernumerary teeth were removed, as earlier suggested. Radiographic evaluation did indicate one supernumerary tooth on the distal of #15 that remained. The orthodontic evaluation revealed a Class 1 crowded relationship with a posterior crossbite, due to severe maxillary contriction. A complete periodontal re-evaluation was performed. Generally speaking, no additional bone loss was noted, however, on the distals of teeth #2,18, and 31, where the impacted teeth had been removed, there was a deficiency in the height of the alveolar ridge of about 50%. There did not appear to be any furcation involvement in the molars greater than Class 1. His case was deemed marginally suitable for treatment by this method of invention.

There was, however, gingival recession and only a thin (facial-lingually) and narrow zone apico-coronally (vertically) of attached fibrotic gingiva on the facials of #20, 21, 22, and 27, and it was determined prudent to perform free gingival grafting in these areas prior to starting the orthodontic work to increase the thickness (facial-lingually) and width (vertically) of the marginal gingiva in this area and lessen the likelihood of additional gingival recession, subsequent to commencing the orthodontic movements. The free gingival grafting was performed under intravenous sedation and local anesthesia. The free gingival grafting was extended to cover the facials of teeth #20, 21, 22, 23, 24, 25, 26, 27, 28 and 29. The donor tissue was removed from the palate and the resulting wounds in the palate were covered with an acrylic stent. The free gingival grafting healed without incident, but the patient did report some significant discomfort and the need to take the narcotic prescription that he was prescribed. The free gingival grafting would have been advisable regardless of which method of orthodontic treatment was selected, be it conventional orthodontics or by this method of invention.

The orthodontic appliances were installed, to include bands on the upper and lower first molars and lower second molars and brackets on all of the other remaining upper and lower teeth. Small diameter light force arch wires were placed and immediately activated. Since the cortical plates around all of the remaining upper and lower teeth would be "activated," the decision was made to perform the surgical portion of this invention at two separate sittings. The upper arch was surgerized at the first sitting and the lower arch was surgerized two days later. One hour prior to the first surgery, the patient premedicated himself with 3 grams of Amoxicillin.

The first surgery was done one day following the completion of the installation and activation of the orthodontic appliances. The surgery was essentially performed in the same manner in both the upper and lower arches. Full thickness (mucoperiosteal) flaps were reflected both facially and lingually around all of the teeth. The "bone activation" was performed both facially and lingually around all of the teeth. This corticotomy preparations consisted of vertical interdental grooves starting just shy of the interdental crest and extending 2 to 3 millimeters beyond the apices of the teeth, and these were connected with connecting horizontal grooves beyond the apices of the teeth. Additionally, pinpoint perforations were performed in the cortical plates directly over the prominences of the roots. The partially decorticated cortical plates were then covered both facially and lingually with a layer of grafting material which consisted of a 50/50 mixture by volume of heat deproteinated bovine bone powder (Osteograf®/N-300) and demineralized freeze dried bone allograft powder. The grafting material was soaked for about 15 minutes in a 10 mg/ml solution of Clindamycin and the excess fluid removed before usage. The full thickness flaps were then returned to their original pre-surgery positions and sutured in place with 3.0 braided black silk interrupted loop sutures. In more recent cases, the braided silk suture material has been discontinued in favor of Gore-tex® suture material. A couple of millimeters of the margins of the flaps were cleared of the grafting material to aid in the reattachment of the flaps to the cervical areas of the teeth. Six milligrams of Decadron was administered after each surgery to lessen post-operative swelling. The patient experienced no discomfort following the surgery in his upper arch and found no need to take the pain medication that he was prescribed.

After the first surgery, the patient was placed on Augmentin, of which he was to take 250 mg three times a day for 10 days. Suturing the flaps back in their original position essentially trapped the grafting material between the under side of the mucoperiosteal flaps and the surface of the partially decorticated (activated) cortical plates. This case is somewhat unique in that all of the major movement in both arches would be accomplished by rather extensive expansion of all of the teeth. There were no anchorage teeth. Most of the teeth would undergo substantial facial movement. The orthodontic appliances were adjusted approximately every 14 days. This included incremental increases in the diameter and strength of the arch wires. The major expansive movements were completed in approximately 4 months. The finer finishing adjustments, which were used to get the bite to "settle-in", required three additional months. The case was completed in about 7 months, from bracketing to de-bracketing, with 12 adjustments having been required. Prior to treatment by the method of this invention, the upper and lower arches were so severely constricted that the patient's facial features were affected, to the extent that his cheeks appeared "caved in".

Only a minimal amount of apical root resorption was noted and there were only a couple of areas with additional gingival recession (1 to 2 millimeters) . There was no apparent decrease in the height of the interdental crestal bone. Lateral cephalometric analysis indicated what appeared to be a new layer of bone of the facials of the upper and lower incisors. A comparison of the pre-treatment CT scan and post-treatment CT scan indicated no dehiscence formation on the facials of any of the remaining upper and lower teeth. The outline of the roots on the post-treatment CT scan is not as obvious as it was on the pre-treatment CT scan, leaving one with the impression of more alveolar bone surrounding the roots of the teeth following treatment than prior to treatment. It is this good alveolar bony support around the roots of the teeth that we anticipate will improve the odds of the case remaining stable. Of particular interest is that the width of the upper arch from the tip of the upper right canine to the tip of the upper left canine was increased by almost 8 mm. This could not have been accomplished with conventional orthodontics without the additional use of orthognathic surgery to expand the upper jaw.

Those skilled in the art will recognize that this invention has been explained with respect to the details, arrangements and steps of certain specific embodiments which have been described and illustrated to explain the nature of this invention. Many modifications can be made to this invention has those skilled in the art without departing from its spirit and scope. Thus, the appended claims are intended to be interpreted to cover such equivalent orthodontic methods and retraction devices which do not depart from the spirit and scope of this invention.

We claim:

1. A method of moving teeth to desired positions within a patient's mouth, comprising:

(a) Installing orthodontic appliances on the teeth to be involved in the orthodontic treatment;

(b) Partially decorticating the cortical bone adjacent the roots of the teeth to be moved;

(c) Inserting grafting material between the partially decorticated cortical bone and overlaying mucoperiosteum; and (d) Adjusting the orthodontic appliances as needed after the foregoing acts to move the teeth toward the desired positions.

2. A method of moving teeth to desired positions within a patient' mouth according to claim 1 wherein grafting material is inserted both facially and lingually between partially decorticated cortical bone and overlaying mucoperiosteum.

3. A method of moving teeth to desired positions within a patient's mouth, comprising:

(a) Installing orthodontic appliances on the teeth to be moved to exert force on the teeth toward the desired positions;

(b) Reflecting full thickness mucoperiosteal flaps to gain access around the teeth to be moved;

(c) After the flaps have been reflected, partially decorticating cortical bone adjacent the roots of the teeth to be moved;

(d) Placing bone grafting material adjacent the partially decorticated cortical bone;

(e) Replacing the mucoperiosteal flaps essentially to their original positions and over the bone grafting material; and (f) Adjusting the orthodontic appliances as needed after the foregoing acts to move the teeth toward the desired positions.

4. A method of retracting teeth to desired positions in an edentulous area within a patient's mouth, comprising:

(a) Installing orthodontic appliances on the teeth to be involved in the orthodontic treatment;

(b) Partially decorticating the cortical bone adjacent the roots of the teeth to be moved;

(c) Performing an osteotomy in the edentulous area;

(d) Inserting grafting material between the partially decorticated cortical bone and overlay mucoperiosteum and in the osteotomised edentulous area;

(e) Installing a retraction device to exert an orthopedic force between teeth being moved and one or more teeth which are not being moved; and (f) Adjusting the retraction device as needed after the foregoing acts to move the teeth toward the desired positions.

5. A retraction device for applying orthopedic forces between anterior teeth and posterior teeth which are separated by at least one edentulous area in the dental arch of a patient, said retraction device comprising, in combination:

(a) A front body and a back body;

(b) A screw member operatively connected between said front body and said back body and adjustable to cause said front body and said back body to move away from one another and to cause said front body and said back body to move toward one another while transmitting an orthopedic force between them;

(c) Only one slide rod extending between said front body and said back body and slidable through at least one of them as said front body and back body move toward and away from another;

(d) Wherein said front body couples solely to at least one anterior tooth and said back body couples solely to at least one posterior tooth so as to transmit an orthopedic force across the at least one edentulous area between the at least one anterior tooth and the at least one posterior tooth as its screw member is adjusted to contract the distance between said front body and said back body.

* * * * *

UNITED STATES PATENT AND TRADEMARK OFFICE
CERTIFICATE OF CORRECTION

PATENT NO.    : 6,109,916
DATED         : August 29, 2000
INVENTOR(S)   : M. Thomas Wilcko and William M. Wilcko It is certified that error appears in the above-identified patent and that said Letters Patent is hereby corrected as shown below:

Column 2,
Line 45, delete "No. Mar. 1, 1996:" and substitute therefor-No. 1, March 1996:--

Column 4,
Line 49, delete "extents" and substitute therefor –extends-

Column 18,
Line 23, delete "c)n" and substitute therefor –on-

Column 20,
Line 53, delete "fall" and substitute therefor –full-

Column 22,
Line 10, delete "or" and substitute therefor –on-

Colum 23,
Line 23, delete "arid" and substitute therefor –and-

Column 24,
Line 14, delete "36" and substitute therefor –35-

Column 25,
Line 50, delete "side" and substitute therefor –slide-

Column 26,
Line 2, delete "834" and substitute therefor –84-

Column 30,
Line 1, delete "booth" and substitute therefor –both-

UNITED STATES PATENT AND TRADEMARK OFFICE
CERTIFICATE OF CORRECTION

PATENT NO. : 6,109,916
DATED : August 29, 2000
INVENTOR(S) : M. Thomas Wilcko and William M. Wilcko It is certified that error appears in the above-identified patent and that said Letters Patent is hereby corrected as shown below:

Column 34,
After line 50, add the following claims:

6. A retraction device according to claim 5 which further includes an extension on at least one of said front body and said back body, said extension having a shape and a position on said at least one of said front body and said back body which inhibits said retaction device from roatating as a result of its screw member being adjusting during use to contract the distance between said front body and said back body.

7. A retratction device for applying orthopedic forces between anterior teeth and posterior teeth which are separated by at least one edentulous area in the dental arch of a patient, said retraction device comprising, in combination:

(a) A front body and a back body;

(b) A screw member operatively connected between said front body and said back body and adjustable to cause said front body and said back body to move away from one another and to cause said front body and said back body to move toward one another while transmitting an orthopedic force between them;

(c) A pair of slide rods extending between said front body and said back body and slidable through at least one of them as said front body and back body move toward and away from another;

(d) Whereing said front body includes a pair of retention arms, each of which couple solely to at least one anterior tooth and said back body includes a pair of retention arms, each of which couples solely to at least one posterior tooth so as to transmit an orthopedic force across the at least one edentulous area between the at least one anterior tooth and the at least one posterior tooth as its screww member is adjusted to contract the distance between said front body and said back body.

UNITED STATES PATENT AND TRADEMARK OFFICE
CERTIFICATE OF CORRECTION

PATENT NO. : 6,109,916
DATED : August 29, 2000
INVENTOR(S) : M. Thomas Wilcko and William M. Wilcko It is certified that error appears in the above-identified patent and that said Letters Patent is hereby corrected as shown below:

8. A method of moving teeth to desired positions within a patient's mouth according to Claim 1 which includes reflecting full thickness mucoperiosteal flaps to gain access around teeth to be moved before partially decorticating the cortical bone, and further includes replacing the mucoperiosteal flaps essentially to their origianl postitions after inserting grafting material between the partially decorticated cortical bone and overlaying mucoperiosteum.

9. A method of moving teeth to desired postitions within a patient's mouth according to Claim 1 in which installing orthodontic appliances on the teeth to be involved in the orthodontic treatment takes place before partially decorticating the cortical bone adjacent the roots of the teeth to be moved and before inserting grafting material between the partially decorticated cortical bone and overlaying mucoperiosteum.

10. A method of moving teeth to desired postitions within a patient's mouth according to Claim 1 in which installing orthodontic appliances on the teeth to be involved in the orthodontic treatment takes place after patially decorticating the cortical bone adjacent the roots of the teeth to be moved and after inserting grafting material between the partially decorticated cortical bone and overlaying mucoperiosteum.

11. A method of moving teeth to desired positions within a patient's mouth according to Claim 3 in which installing orthodontic appliances on the teeth to be moved takes place before reflecting full thickness mucoperiosteal flaps, before partially decortticating cortical bone, before placing bone grafting material adjacent the partially decorticated cortical bone, and before replacing the mucoperiosteal flaps essentially to their original positions.

12. A method of moving teeth to desired postitions within a patient's mouth according to Claim 3 in which installing orthodontic appliances on the teeth to be moved takes place after reflecting full thickness mucoperiosteal flaps, after partially decorticating cortical bone, after placing bone grafting material adjacent the partially decorticated cortical bone, and after replacing the mucoperiosteal flaps essentially to their original positions.

UNITED STATES PATENT AND TRADEMARK OFFICE
CERTIFICATE OF CORRECTION

PATENT NO. : 6,109,916
DATED : August 29, 2000
INVENTOR(S) : M. Thomas Wilcko and William M. Wilcko It is certified that error appears in the above-identified patent and that said Letters Patent is hereby corrected as shown below:

13. A method of retracting teeth to desired positions in an edentulous area according to Claim 4 which includes reflecting full thickness mucoperiosteal flaps to gain access around teeth to be moved, before partially decorticating the cortical bone and further includes replacing the mucoperiosteal flaps essentially to their original positions after inserting grafting material between the partially decorticated cortical bone and overlaying mucoperiosteum.

14. A method of retracting teeth to desired postitions in an edentulous area within a patient's mouth according to Claim 4 in which installing orthodontic appliances on teeth to be moved takes place before partially decorticating the cortical bone, before performing an osteotomy in the edentulous area, before inserting grafting material between the partially decorticated cortical bone and the overlaying mucoperiosteum, before installing a retraction device, and before adjusting the retraction device.

15. A method of retracting teeth to desired positions in an edentulous area within a patient's mouth according to Claim 4 in which installing orthodontic appliances on the teeth takes place after partially decorticating the cortical bone, after performing an osteotomy in the edentulous area, after inserting grafting material between the cortical bone, after performing an osteotomy in the edentulous area, after inserting grafting material between the partially decorticated cortical bone and the overlaying mucoperiosteum, but before installing a retraction device.

Signed and Sealed this

Fourteenth Day of August, 2001

*Attest:*

*Attesting Officer*

NICHOLAS P. GODICI
*Acting Director of the United States Patent and Trademark Office*

UNITED STATES PATENT AND TRADEMARK OFFICE
CERTIFICATE OF CORRECTION

PATENT NO. : 6,109,916
DATED : August 29, 2000
INVENTOR(S) : M. Thomas Wilcko and William M. Wilcko It is certified that error appears in the above-identified patent and that said Letters Patent is hereby corrected as shown below:

Column 2,
Line 45, delete "No. Mar. 1, 1996:" and substitute therefor–No. 1, March 1996:--

Column 4,
Line 49, delete "extents" and substitute therefor –extends-

Column 18,
Line 23, delete "c)n" and substitute therefor –on-

Column 20,
Line 53, delete "fall" and substitute therefor –full-

Column 22,
Line 10, delete "or" and substitute therefor –on-

Colum 23,
Line 23, delete "arid" and substitute therefor –and-

Column 24,
Line 14, delete "36" and substitute therefor –35-

Column 25,
Line 50, delete "side" and substitute therefor –slide-

Column 26,
Line 2, delete "834" and substitute therefor –84-

Column 30,
Line 1, delete "booth" and substitute therefor –both-

UNITED STATES PATENT AND TRADEMARK OFFICE
CERTIFICATE OF CORRECTION

PATENT NO. : 6,109,916
DATED : August 29, 2000
INVENTOR(S) : M. Thomas Wilcko and William M. Wilcko It is certified that error appears in the above-identified patent and that said Letters Patent is hereby corrected as shown below:

Column 34,
After line 50, add the following claims:

6. A retraction device according to claim 5 which further includes an extension on at least one of said front body and said back body, said extension having a shape and a position on said at least one of said front body and said back body which inhibits said retaction device from rotating as a result of its screw member being adjusted during use to contract the distance between said front body and said back body.

7. A retraction device for applying orthopedic forces between anterior teeth and posterior teeth which are separated by at least one edentulous area in the dental arch of a patient, said retraction device comprising, in combination:

(a) A front body and a back body;

(b) A screw member operatively connected between said front body and said back body and adjustable to cause said front body and said back body to move away from one another and to cause said front body and said back body to move toward one another while transmitting an orthopedic force between them;

(c) A pair of slide rods extending between said front body and said back body and slidable through at least one of them as said front body and back body move toward and away from another;

(d) Wherein said front body includes a pair of retention arms, each of which couple solely to at least one anterior tooth and said back body includes a pair of retention arms, each of which couples solely to at least one posterior tooth so as to transmit an orthopedic force across the at least one edentulous area between the at least one anterior tooth and the at least one posterior tooth as its screw member is adjusted to contract the distance between said front body and said back body.

UNITED STATES PATENT AND TRADEMARK OFFICE
CERTIFICATE OF CORRECTION

PATENT NO.    : 6,109,916
DATED         : August 29, 2000
INVENTOR(S)   : M. Thomas Wilcko and William M. Wilcko It is certified that error appears in the above-identified patent and that said Letters Patent is hereby corrected as shown below:

8. A method of moving teeth to desired positions within a patient's mouth according to Claim 1 which includes reflecting full thickness mucoperiosteal flaps to gain access around teeth to be moved before partially decorticating the cortical bone, and further includes replacing the mucoperiosteal flaps essentially to their original positions after inserting grafting material between the partially decorticated cortical bone and overlaying mucoperiosteum.

9. A method of moving teeth to desired positions within a patient's mouth according to Claim 1 in which installing orthodontic appliances on the teeth to be involved in the orthodontic treatment takes place before partially decorticating the cortical bone adjacent the roots of the teeth to be moved and before inserting grafting material between the partially decorticated cortical bone and overlaying mucoperiosteum.

10. A method of moving teeth to desired positions within a patient's mouth according to Claim 1 in which installing orthodontic appliances on the teeth to be involved in the orthodontic treatment takes place after partially decorticating the cortical bone adjacent the roots of the teeth to be moved and after inserting grafting material between the partially decorticated cortical bone and overlaying mucoperiosteum.

11. A method of moving teeth to desired positions within a patient's mouth according to Claim 3 in which installing orthodontic appliances on the teeth to be moved takes place before reflecting full thickness mucoperiosteal flaps, before partially decorticating cortical bone, before placing bone grafting material adjacent the partially decorticated cortical bone, and before replacing the mucoperiosteal flaps essentially to their original positions.

12. A method of moving teeth to desired postitions within a patient's mouth according to Claim 3 in which installing orthodontic appliances on the teeth to be moved takes place after reflecting full thickness mucoperiosteal flaps, after partially decorticating cortical bone, after placing bone grafting material adjacent the partially decorticated cortical bone, and after replacing the mucoperiosteal flaps essentially to their original positions.

UNITED STATES PATENT AND TRADEMARK OFFICE
CERTIFICATE OF CORRECTION

PATENT NO. : 6,109,916
DATED : August 29, 2000
INVENTOR(S) : M. Thomas Wilcko and William M. Wilcko It is certified that error appears in the above-identified patent and that said Letters Patent is hereby corrected as shown below:

13. A method of retracting teeth to desired positions in an edentulous are according to Claim 4 which includes reflecting full thickness mucoperiosteal flaps to gain access around teeth to be moved, before partially decorticating the cortical bone and further includes replacing the mucoperiosteal flaps essentially to their original positions after inserting grafting material between the partially decorticated cortical bone and overlaying mucoperiosteum.

14. A method of retracting teeth to desired positions in an edentulous area within a patient's mouth according to Claim 4 in which installing orthondontic appliances on teeth to be moved takes place before partially decorticating the cortical bone, before performing an osteotomy in the edentulous area, before inserting grafting material between the partially decorticated cortical bone and the overlaying mucoperiosteum, before installing a retraction device, and before adjusting the retraction device.

15. A method of retracting teeth to desired positions in an edentulous area without a patient's mouth according to Claim 4 in which installing orthondontic appliances on the teeth takes place after partially decorticating the cortical bone, after performing an osteotomy in the edentulous area, after inserting grafting material between the partially decorticated cortical bone and the overlaying mucoperiosteum, but before installing a retraction device.

This Certificate supercedes Certificate of Correction, issued August 14, 2001

Signed and Sealed this

Thirtieth Day of October, 2001

Attest:

NICHOLAS P. GODICI
Attesting Officer
Acting Director of the United States Patent and Trademark Office